United States Patent
McCafferty

(10) Patent No.: US 11,026,576 B2
(45) Date of Patent: Jun. 8, 2021

(54) REDUCING ERRORS OF TONOMETRIC MEASUREMENTS BY USING A TONOMETER TIP WITH A CURVED CORNEA-CONTACTING SURFACE

(71) Applicant: CATS TONOMETER, LLC, Tucson, AZ (US)

(72) Inventor: Sean J. McCafferty, Tucson, AZ (US)

(73) Assignee: CATS TONOMETER, LLC, Tucson, AZ (US)

(*) Notice: Subject to any disclaimer, the term of this patent is extended or adjusted under 35 U.S.C. 154(b) by 238 days.

(21) Appl. No.: 16/000,573

(22) Filed: Jun. 5, 2018

(65) Prior Publication Data

US 2018/0296090 A1 Oct. 18, 2018

Related U.S. Application Data

(63) Continuation-in-part of application No. 15/565,244, filed as application No. PCT/US2015/047134 on Aug. 27, 2015, now abandoned.
(Continued)

(51) Int. Cl.
*A61B 3/16* (2006.01)
*A61B 3/00* (2006.01)
(Continued)

(52) U.S. Cl.
CPC .............. *A61B 3/16* (2013.01); *A61B 3/0025* (2013.01); *A61B 3/107* (2013.01); *A61B 3/14* (2013.01); *A61B 2560/0276* (2013.01)

(58) Field of Classification Search
CPC .. A61B 3/16; A61B 3/107; A61B 3/10; A61B 3/0025; A61B 3/14; A61B 2560/0276
See application file for complete search history.

(56) References Cited

U.S. PATENT DOCUMENTS 3,952,585 A * 4/1976 Perkins ..................... A61B 3/16
                                                                   600/405
5,031,622 A * 7/1991 LaHaye ................... A61B 3/16
                                                                   206/316.1
(Continued)

FOREIGN PATENT DOCUMENTS

JP    2003111732    3/2015
NL      7408214    12/1975
(Continued)

OTHER PUBLICATIONS

Kaufmann et al. 'Comparison of Dynamic Contour Tonometry with Goldmann Applanation Tonometery'; Investigative Ophthalmology & Visual Science, Sep. 2004, vol. 45, No. 9 (Year: 2004).*
(Continued)

*Primary Examiner* — Patrick Fernandes
(74) *Attorney, Agent, or Firm* — Yakov Sidorin; Quarles & Brady LLP

(57) ABSTRACT

A device including a contact tonometer tip having a bi-curved cornea-contacting surface structured to reduce, during the tonometric measurement, at least the measurement error caused by the presence of a fluid film between the tip and the cornea and/or the intra-corneal stress formed during the applanation deformation and occurring at a location of the tip-to-cornea contact area. Method for using such device for measurement of intraocular pressure while procuring values IOP with increased accuracy as compared to those obtained with the use of a conventional flat-surface tonometer tip. The cornea-contacting surface includes a first central portion and a second portion that encircles and adjoins the first central portion. The curvatures of the first and second portions have opposite signs. In one case, the first central portion has a curvature with the same sign as that of the cornea and/or is rotationally-symmetric.

20 Claims, 23 Drawing Sheets

Related U.S. Application Data

(60) Provisional application No. 62/658,273, filed on Apr. 16, 2018, provisional application No. 62/597,714, filed on Dec. 12, 2017, provisional application No. 62/148,048, filed on Apr. 15, 2015.

(51) Int. Cl.
*A61B 3/107* (2006.01)
*A61B 3/14* (2006.01)

(56) References Cited

U.S. PATENT DOCUMENTS

| | | | |
|---|---|---|---|
| 5,032,020 | A | 7/1991 | Robert |
| 5,577,026 | A | 11/1996 | Gordon et al. |
| 5,814,900 | A | 9/1998 | Esser et al. |
| 8,556,823 | B2 | 10/2013 | Koest et al. |
| 2013/0144185 | A1* | 6/2013 | Fuller ............... A61B 5/031 600/561 |
| 2013/0211285 | A1 | 8/2013 | Fuller et al. |
| 2014/0073897 | A1* | 3/2014 | McCafferty ............ A61B 3/16 600/399 |
| 2016/0029888 | A1 | 2/2016 | Maggiano et al. |
| 2017/0023486 | A1 | 1/2017 | Wang et al. |

FOREIGN PATENT DOCUMENTS

| | | |
|---|---|---|
| WO | 2006087715 A2 | 8/2006 |
| WO | 2016167827 A1 | 10/2016 |

OTHER PUBLICATIONS

International Search Report and Written Opinion in related International Application No. PCT/US2015/047134, dated Feb. 1, 2016, 14 pages.

Nissen, O. I., "Bilateral Recording of Human Intraocular Pressure with an Improved Applanting Suction Cup Tonograph," Department of Medical Physiology, University of Copenhagen and Department of Opthalmology, Nov. 15, 1979, pp. 377-387.

International Search Report and Written Opinion in related International Application No. PCT/US2018/064878, dated Mar. 21, 2019, 15 pages.

* cited by examiner

REDUCING ERRORS OF TONOMETRIC MEASUREMENTS BY USING A TONOMETER TIP WITH A CURVED CORNEA-CONTACTING SURFACE

CROSS-REFERENCE TO RELATED APPLICATIONS

The present application claims priority from and benefit of the U.S. Provisional Patent Applications No. 62/597,714 filed on Dec. 12, 2017 and No. 62/658,273 filed on Apr. 16, 2018.

The present application is also a continuation-in-part from the U.S. patent application Ser. No. 15/565,244 filed on Oct. 9, 2017, which is a national phase of the International Patent Application No. PCT/US2015/047134 fled on Aug. 27, 2015, which is turn claims priority from the U.S. Provisional Patent Application No. 62/148,048, filed on Apr. 15, 2015.

The disclosure of each of the above-referenced applications is incorporated herein by reference.

TECHNICAL FIELD

The present invention relates to tonometry-based measurements of intraocular pressure (IOP) of an eye and, more particularly, to tonometry performed with an applanation tonometer system (such as, for example, the Goldman tonometer) equipped with a tonometer tip (or simply tip, for short) that has the cornea-contacting (applanating) surface judiciously-curved to reduce errors contributed to the conventionally-performed measurements by various eye-related factors.

The conventionally used contact tonometer system (such as, for example, a Goldmann applanation tonometer presented schematically in FIG. 1B and discussed further below) utilizes a flat, planar surface tip (that is the tip, a cornea-contacting surface of which has a zero curvature and is substantially perpendicular to the axis of the tip, see FIG. 1A. Such tip may be interchangeably referred to below as GAT tonometer tip, or GAT tonometer prism, or flat-surfaces tonometer tip or prism). The use of the conventionally-structured tonometer tip is well established and widely used, on the one hand, and, on the other hand, are known to inevitably require post-measurement corrections (of the results of the measurements of the intraocular pressure in the eye) to account for eye-related factors. It is also well recognized that the accuracy of such correction is often questionable, as the post-measurement corrections—if used at all—are predicated on the unpredictable degree of correlation among the error-contributing factors in light of the geometry of the cornea-applanating surface of the conventionally-configured tip. There remains a need, therefore, in a different methodology of performing tonometric measurements of the IOP that would allow the user to alleviate—if not remove completely—the need for correcting the results of the measurements of the intraocular pressure, or, at least, to ensure that the introduced correction(s) are sufficiently precise to reduce conventional errors.

SUMMARY

The idea of the invention stems from the realization that the above-mentioned drawback of the conventionally-used contact tonometer is caused, in significant part, by the use of the flatly-shaped tonometer tip. As a non-limiting example, discussed in detail below, the contribution of the non-zero curvature of the cornea to the errors of the IOP measurement (or, in another example, the contribution of the error due to the tear-film-caused adhesion between the tonometer tip's surface and the corneal surface) is neither compensated by the existing tonometer tip(s) nor addressed by the related art: the difference between the curvatures of the flat tonometer tip (zero curvature) and a non-zero curvature cornea cases a ripple or kink in the surface of cornea during the applanation procedure, which significantly distorts the corneal surface, causing intra-corneal stress that, in turn, adds errors to the measurement of the IOP. At the same time, in this example, the cornea with non-zero curvature forms a component of force transferred to the tonometer tip and even further obscuring IOP measurement.

False measurement of the IOP with the existing tonometer tip (the exact amount of required corrections for which remains very uncertain—creates a risk for misdiagnosis and/or delayed detection of ophthalmological diseases.

These drawbacks of the conventional measurement of the IOP with the use of a flat-surfaced tonometer tip are resolved by contraptions of the present invention. In particular, a persisting problem of the need for a largely-undefined correction of the results of an IOP measurement performed with an applanation tonometer is solved by providing a tonometer with a tip the cornea-contacting surface of which is judiciously curved and not flat. Equipping the tonometer tip's surface with a specifically-defined curvature as discussed reduces and, in some cases, eliminates measurement errors caused by corneal curvature and intracorneal stress, thereby allowing a user to rely on raw results of direct IOP measurement carried out with the tonometer tip of the invention.

Embodiments of invention provide a method for measurement of intraocular pressure (IOP) with a contact tonometer. The method includes the step of pressing an axial portion of a cornea-contacting curvilinear surface of a first tonometer tip against cornea of an eye to apply force to the cornea and to define a first surface of contact between the curvilinear surface. (Here, the first tonometer tip has a first axis and the cornea has a corneal axis). The method further includes the step of forming a first image of the first surface of contact in light transmitted twice through the first tonometer tip and reflected from the cornea, the first image including first and second substantially semicircular portions; and a step of adjusting the force applied by the first tonometer tip to the cornea to achieve a condition when adjacent ends of the first and second semicircular portions substantially coincide. Here, such condition is or can be achieved only when an axis of the first tonometer tip and an axis of the cornea substantially coincide. If the condition is not achieved, the method additionally includes the step of realigning the curvilinear surface with respect to the cornea and repeating the step of adjusting the force. The step of pressing may include pressing the axial portion of the cornea-contacting curvilinear surface that has a first curvature with a first sign of curvature equal to a second sign of curvature (the second sign of curvature being equal to a sign of curvature of the cornea). Alternatively or in addition, the method may include a step of reversibly changing a surface area of the first surface of contact as a result of the adjusting the force and/or a step of determining a first value of the IOP with the use of the first image (at a moment when the adjacent ends substantially coincide such that a first error is smaller than a second error. Here, the first error is an error contributed to the first value by any of a corneal rigidity, corneal thickness, corneal curvature, misalignment between the first axis and the corneal axis, and an effect produced by presence of a film of fluid between the cornea-contacting curvilinear surface, while the second error represents an error contributed to a second value of the IOP measured with a contact tonometer equipped with a second tonometer tip (the second tonometer tip having a planar cornea-contacting surface). In a specific case, the step of pressing may include causing first intra-ocular stress at a location of the cornea as a result of applanation of the cornea at the first surface of contact, where a first value of the first intra-ocular stress is smaller than a second value of second intra-ocular stress that occurs at the location as a result of applanation of the cornea with a second tonometer tip by applying the same pressure to the cornea with a planar cornea-contacting surface of the second tonometer tip. In a related embodiment, the step of pressing may alternatively or in addition include applying the force to define a first averaged angle of contact between the cornea-contacting curvilinear surface and the cornea, where the first averaged angle of contact is at least twice as big as a second averaged angle of contact. Here, the second averaged angle of contact is an angle of contact formed, as a result of applying the force to the cornea by bringing a planar cornea-contacting surface of a second tonometer tip in contact with the cornea.

Embodiments of the invention also provide a device configured for determining intraocular pressure (IOP) of an eye with the use of contact tonometry. The device includes a first tonometer tip that has a first axis; a front surface having a central portion that is non-planar and has a non-zero curvature, and that is configured to applanate the cornea of the eye to form the applanated portion of the cornea when pressed against the cornea while, at the same time, reducing a first error as compared with a second error. (Here, the cornea has a corneal axis; the first error is an error contributed to a first value of determined IOP of the eye by adhesion between the front surface and the cornea, the second error is an error contributed to a second value of the IOP measured with the use of a second tonometer tip that has a planar cornea-contacting surface, and the adhesion is caused by a film of fluid present between the front surface and the cornea). The first tonometer tip additionally contains a back surface that is substantially transverse to the first axis. The device may further include a system of optical prisms in a body of the first tonometer tip, disposed to form an image of the applanated portion of the cornea in light transmitted through the front surface and through the system of the optical prisms (where the image contains a first semicircle having a first end and a second semicircle having a second end, and where the first and second ends substantially coincide only when the first axis and the corneal axis substantially coincide). Alternatively or in addition, the front surface is dimensioned to applanate the cornea, when pressed against the cornea, while reducing a third error as compared with a fourth error. Here, the third error is an error contributed to the first value of the determined IOP by any of curvature of the cornea, thickness of the cornea, corneal rigidity, and misalignment between the first axis and the corneal axis. The fourth error is an error contributed to the second value of the IOP. Alternatively or in addition, a sign of the non-zero curvature may be equal to a sign of a curvature of the cornea; and/or a reduction of the first error, contributed to the first value of the determined IOP of the eye by the adhesion, is at least 10 percent. Alternatively or in addition, the front surface includes an annular portion that circumscribes the central portion. (Here, the annular portion tangentially merging with the central portion along a closed curve; the annular portion defining an axially-symmetric curve, in a surface of the annular portion that contains a plurality of vertices of the annular portion. The diameter of the axially-symmetric curve defines a maximum extent of the applanated portion of the cornea that can be achieved without forming a spatial kink in the cornea.) In a specific implementation of the latter embodiment, the closed plane curve is defined in a plane that is transverse to the first axis. In a related implementation, the front surface includes a surface portion congruent with a portion of a spherical surface, and such surface portion is devoid of openings through the surface. In yet another related embodiment, the front surface is made an azimuthally symmetric bi-curved surface having a cross-section, in a plane containing the first axis, that is defined by an axially-monotonic curve with a second derivative defined at every point of the axially-monotonic curve. In any implementation, the device may be configured as an applanating tonometer and comprise a source of light positioned to transmit light through optical prisms, disposed in a body of the first tonometer tip, towards the front surface.

Embodiments of the invention additionally provide a device configured for determining intraocular pressure (IOP) of an eye with the use of contact tonometry. Such device includes a first tonometer tip having a first axis and a front surface. The front surface contains a central portion that is non-planar, has a non-zero curvature, and is configured to applanate the cornea of the eye (the cornea having a corneal axis) to form the applanated portion of the cornea when pressed against the cornea while having a first error reduced as compared with a second error. The first error is an error contributed to a first value of the IOP of the eye by adhesion between the front surface and the cornea, the first value being a value of the IOP tonometrically determined with the use of said tonometer tip. The second error is an error contributed to a second value of the IOP measured with the use of a second tonometer tip that has a planar cornea-contacting surface. The adhesion is caused by a film of fluid present between the front surface and the cornea. The central portion has a first curvature with a first sign, the cornea has a curvature of the cornea with a second sign, and the first sign is equal to the second sign.

In one implementation, the front surface is dimensioned to applanate the cornea of the eye, when pressed against the cornea, while reducing a third error as compared with a fourth error. Here, the third error is an error contributed to the first value of the determined IOP by any of the curvature of the cornea, a thickness of the cornea, corneal rigidity, and misalignment between the first axis and the corneal axis. The fourth error is an error contributed to the second value of the IOP with the use of the tonometer tip that has the planar cornea-contacting surface. Alternatively or in addition, the front surface further includes an annular portion surrounding the central portion and tangentially merging with the central portion along a closed plane curve, the annular portion having a curvature with a third sign, the third sign being opposite to the first sign. In this latter case, the annular portion may contain an axially-symmetric curve in a surface of the annular portion. (Such axially-symmetric curve defined by a plurality of vertices of the annular portion, and the diameter of the axially-symmetric curve defines a maximum extent of the applanated portion of the cornea that can be achieved without forming a spatial kink in the corneal surface.) The front surface may be axially-symmetric and, in a specific case, rotationally symmetric. Alternatively or in addition, the front surface may be an azimuthally symmetric bi-curved surface having a cross-section, in a plane containing the first axis that is defined by a spatially-monotonic curve with a second derivative defined at every point of said spatially-monotonic curve. Alternatively or in addition, the device may include a system of optical prisms in a body of the first tonometer tip, disposed to form an image of the applanated portion of the cornea in light transmitted through the front surface and through the system of the optical prisms. In this case, the image contains a first semicircle having a first end and a second semicircle having a second end, and the first and second ends substantially coincide only when the first axis and the corneal axis substantially coincide. The device may be configured as a contact tonometer and, in a specific case, as an optical applanating tonometer (for example, the tonometer operating according to the principle of operation of Goldmann applanation tonometer).

Embodiments further provide a method for measurement of intraocular pressure (TO) with a contact tonometer. The method includes:—applying force to the cornea of an eye by bringing an axial portion of a cornea-contacting curvilinear surface of a first tonometer tip in contact with the cornea i) to define a first surface of contact between the curvilinear surface and the cornea and ii) to cause first intra-corneal stress at a location of the cornea as a result of applanation of the cornea at the first surface. Here, the first tonometer tip has a first axis and the cornea has a corneal axis;—forming a first image of the first surface of contact in light transmitted twice through the first tonometer tip and reflected from the cornea; and—tonometrically measuring a first value of the IOP with the use of the first image (while the axial portion has a first curvature having a first sign of curvature that is equal to a sign of curvature of the cornea, and while a first value of the first intra-corneal stress is smaller than a second value of second intra-corneal stress that occurs at said location as a result of applanation of the cornea with a second tonometer tip by applying the same force to the cornea with a flat cornea-contacting surface of the second tonometer tip).

The process of measuring may include measuring the first value with a first error that is smaller than a second error. Here, the first error is contributed to the first value by any of corneal rigidity, corneal thickness, corneal curvature, misalignment between the first axis and the corneal axis, and an effect produced by presence of a film of fluid between the cornea-contacting curvilinear surface and the cornea. The second error, at the same time, represents an error contributed to a second value of the IOP measured with an applanating tonometer that is equipped with the second tonometer tip while applying the same force to the cornea with the flat cornea-contacting surface of the second tonometer tip. Alternatively or in addition, the process of measuring may include measuring the first value with a first error, the first error representing an error contributed to such first value only by the presence of a tear-film between the cornea-contacting curvilinear surface and the cornea. (In this latter specific case, a difference between the second and first errors represents a reduction of a capillary force, formed by the tear-film, by at least 10 percent as compared with that formed by the tear-film during a process of measuring the second value of the IOP with the use of the second tonometer tip while applying the same force to the cornea by bringing the flat cornea-contacting surface of the second tonometer tip in contact with the cornea.) Alternatively or in addition, the formation of force applied to the cornea may be caused by bringing the axial portion of a cornea-contacting curvilinear surface of the first tonometer tip in contact with the cornea to define a first averaged angle of contact between the cornea-contacting curvilinear surface and the cornea. (Here, the first averaged angle of contact is at least twice as big as a second averaged angle of contact; and the second averaged angle of contact is an averaged angle of contact formed between the flat cornea-contacting surface of the second tonometer tip and the cornea, formed as a result of applying the same force to the cornea by bringing said flat cornea-contacting surface in contact with the cornea.)

In a specific embodiment, the process of measuring may include measuring the first value with a first error, the first error representing an error contributed by corneal curvature, where an absolute value of the first error smaller than an absolute value of a second error by at least 1 mmHg, and where the second error represents an error contributed by the corneal curvature to a second value of the IOP measured with the use of the second tonometer tip while applying the same force to the cornea by bringing the flat cornea-contacting surface of the second tonometer tip in contact with the cornea. In a related specific embodiment, the process of measuring may include measuring the first value with a first error, the first error representing an error contributed by corneal thickness. Here, an absolute value of the first error is smaller than an absolute value of a second error by at least 1 mmHg, and the second error represents an error contributed by the corneal thickness to a second value of the IOP measured with the use of the second tonometer tip while applying the same force to the cornea by bringing the flat cornea-contacting surface of the second tonometer tip in contact with the cornea. In yet another specific embodiment, the process of measuring includes measuring the first value with a first error, the first error representing an error contributed by corneal rigidity, where an absolute value of the first error is smaller than an absolute value of a second error by at least 1 mmHg, and where the second error represents an error contributed by the corneal rigidity to a second value of the IOP measured with the use of the second tonometer tip while applying the same force to the cornea by bringing the flat cornea-contacting surface of the second tonometer tip in contact with the cornea.

In substantially any implementation of the method, the process of forming the image may include forming the first image containing first and second semicircular portions, and adjusting the force to achieve a condition when adjacent ends of the first and second semicircular portions coincide, where such condition can be achieved only when the first axis and the corneal axis coincide. Alternatively or in addition, any implementation of the method may include a step of reversibly changing a surface area of the first surface of contact as a result of applying the force to the cornea.

BRIEF DESCRIPTION OF THE DRAWINGS

The invention will be more fully understood by referring to the following Detailed Description in conjunction with the generally not-to-scale Drawings, of which:

FIG. 14A: a schematic of the tonometer tip in contact with the corneal surface and the direction of the adhesion force formed by the tear-film. FIG. 14B: illustration of the tear-film meniscus and angle $\theta$ between the cornea and applanation surface of the tonometer prism. FIG. 14C: illustration of applanation mires imaged through the tonometer prism, demonstrating mire thickness and measurement applanation endpoint.

Figure 1A:
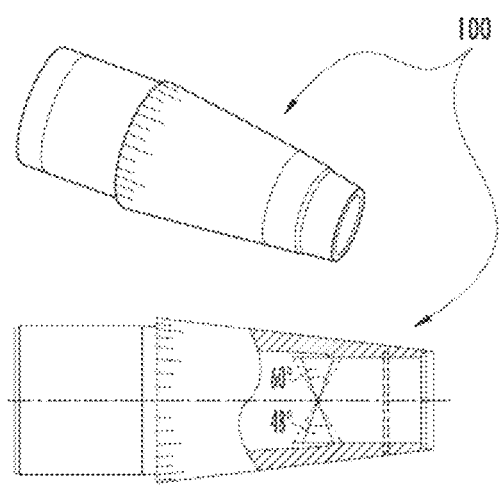
FIG. 1A presents two views of a conventionally-shaped Goldmann applanation tonometer tip used for measurements of a human eye (a cut-out of one view showing the bi-prism with an angle of 60 degrees)

Generally, the sizes and relative scales of elements in Drawings may be set to be different from actual ones to appropriately facilitate simplicity, clarity, and understanding of the Drawings. For the same reason, not all elements present on one Drawing may necessarily be shown in another.

DETAILED DESCRIPTION

The discussed implementations of the idea of invention address problems accompanying the measurements of intraocular pressure in the eye that are conventionally performed with the use of a Goldmann-type applanation tonometer (GAT) having a tip with a flat, planar cornea-contacting surface. The embodiments further facilitate such measurements by nullifying, in some cases, the need to correct the results of the measurements for the contribution of corneal thickness and stiffness (and/or other characteristics of the eye), while at the same time minimizing both the error of the IOP-measurement caused by the corneal curvature, corneal rigidity, and the intraocular stress imposed on the eye-ball my the measurement procedure but ignored clinically to-date. Such advantageous effects are achieved by employing a tonometer tip having the cornea-contacting (generally axially symmetric) surface configured to include at least i) a central curved portion and ii) a peripheral portion encircling the central portion having a curvature with a sign opposite to the sign of the curvature of the central portion. The central and peripheral portions of the tonometer tip surface are configured to merge tangentially along a closed plane curve.

Counterintuitively, in one embodiment of the invention in which the sign of the curvature of the cornea-contacting surface of the tip has the same sign as that of the cornea, making the applanation surface of the tip geometrically-matching and congruent with the surface of the cornea should be avoided, as such substantially perfect geometrical matching would cause the applanation area of the cornea to be met with zero force from the tonometer tip (during the IOP measurement), thereby negating the very idea of the measurement itself and rendering the measurement substantially useless. The term congruent, when used in reference to chosen first and second elements, specifies that these elements coincide at substantially all points when superimposed. Accordingly, an embodiment of a method of the invention may include a step of reversibly changing a surface area of the surface of contact between the cornea-contacting curved surface (of an embodiment of the tonometer tip) and the cornea, as a result of adjusting a force applied by the embodiment of the tonometer tip to the cornea, while the cornea-contacting curved surface is not substantially congruent with the surface of the cornea. (A person of skill will readily appreciate that the lack of perfect congruency and/or geometrical matching between the cornea-contacting surface of an embodiment of the tonometer tip is specifically distinct, both structurally and functionally from, for example, the substantially perfect congruency and/or geometrical matching between the cornea-contacting surface of a contact lens and the cornea. Indeed, in the latter case the congruency and geometrical matching is required and present exactly because otherwise the optical performance of the contact lens, dimensioned to correct the imperfect vision of the eye, cannot be carried out and/or achieved. Incidentally, the change of force applied through the contact lens to the cornea does not result in a change of a surface area across which the contact lens and the cornea are in physical contact. Furthermore, the operational contact between a surface, dimensioned according to the shape of the cornea-contacting surface of the contact lens, and the cornea simply does not result in any applanation of the cornea.)

Counterintuitively—and to a noticeable advantage (over the conventional design of a tonometer member having a tip with a flat, not curved surface) at least in terms of minimization of intracorneal stress during the measurement—the curvature of the central portion of the surface of the tip of one specific embodiment preferably has a sign opposite to that of the curvature of the cornea. In accordance with embodiments of the present invention, methods and apparatus are disclosed for an ophthalmological instrument including a corneal contact member structured according to the idea of the invention for use with the GAT platform. Embodiments of the invention include a tonometer tip, containing a biprism-containing portion and a corneal contact surface the shape of which that is configured to minimize deformation of the corneal surface and the intracorneal stress during measurement of the intraocular pressure.

For the purposes of this disclosure and the appended claims, and unless stated otherwise:

A plane curve is a curve defined in a plane. A closed plane curve is a curve with no end points and which completely encloses an area. Preferably, the closed plane curve is defined in a plane that is transverse to the axis, that is in a plane that is lying or extending across (or in a cross direction) with respect to the axis and in a specific case—in a plane that extends orthogonally to the axis. This enhances homogeneity of deformation of the cornea when the corneal contact surface portion of the corneal contact member is being pressed against the cornea.

Generally, a surface of the corneal contact member (i.e., a tonometer tip_ has a surface that deviates from a flat surface to reduce sensitivity of the IOP measurement to biomechanical parameters of the cornea and the presence of the tear-film, and that includes two surface portions curved differently, one being a concave surface portion and another being a convex surface portion. For the purposes of this disclosure and appended claims, terms such as radius of curvature, curvature, sign of curvature and related terms are identified according to their mathematical meanings recognized and commonly used in related art. For example, a radius of curvature of a given curve at a point at the curvemi is defined, generally, as a radius of a circle that most nearly approximates the curve at such point. The term "curvature" refers to the reciprocal of the radius of curvature. A definition of a curvature may be extended to allow the curvature to take on positive or negative values (values with a positive or negative sign). This is done by choosing a unit normal vector along the curve, and assigning the curvature of the curve a positive sign if the curve is turning toward the chosen normal or a negative sign if it is turning away from it. For the purposes of the present disclosure and the accompanying claims, a sign of a given curvature is defined according to such convention. For definitions of these and other mathematical terms, a reader is further referred to a standard reference text on mathematics such as, for example, I. N. Bronstein, K. A. Semendyaev, Reference on Mathematics for Engineers and University Students, Science, 1981 (or any other edition).

The term "surface" is used according to its technical and scientific meaning to denote a boundary between two media or bounds or spatial limits of a tangible element; it is understood as that which has length and breadth but not thickness, a skin (with a thickness of zero) of a body.

The terms "applanation", "applanate", "flattening", "flatten" and the like generally refer to a process of action as a result of which a surface curvature of a subject at hand is being reduced, that is, the surface is being flattened or applanated (resulting in a surface the curvature of which is at least reduced as compared to the initial value of curvature and/or, in a specific case, resulting in a surface that is substantially flat or planar).

General Considerations

Tonometry is a non-invasive procedure that eye-care professionals perform to determine the intraocular pressure, the fluid pressure inside the eye. It is an important test in the evaluation of patients at risk from glaucoma, a disease often causing visual impairment in a patient. In applanation tonometry the intraocular pressure is inferred from the force required to flatten (applanate) a constant, pre-defined area of the cornea, as per the Imbert-Fick hypothesis that holds that when a flat surface is pressed against a closed sphere with a given internal pressure, an equilibrium will be attained when the force exerted against the spherical surface is balanced by the internal pressure of the sphere applied over the area of contact. In other words, pressure P within a flexible, elastic (and presumably infinitely thin) sphere is approximately equal to the external force f required to flatten a portion of the sphere and normalized by an area A that is flattened, P=f/A. Accordingly, a transparent pressure member (GAT tip element) with a planar contact surface (such as the element 100 as shown in FIG. 1A, for example) is pressed against the cornea of an eye in such a way that the latter is flattened over a pre-determined area (that in practice is about 7.3 mm$^2$).

The Imbert-Fick principle, shown in Equation (1), states that the reaction force of the eye, F, is a linear function of the IOP, P. (Based on the Imbert-Fick principle, the applied-force-to-pressure conversion conventionally assumes that the IOP is uniquely responsible for the force required to applanate the cornea.) The reaction force also depends on the force required to deform the cornea tissue, T, and the cross-sectional contact area of the tonometer surface, A. In this study, the normal IOP, $P_0$, was considered to by 16.0 mmHg.

$$F(P)=T(\delta)+PA(\delta) \quad (1)$$

The contact area is a function of the depth of displacement of the cornea, δ, along the axis of the tonometer tip caused as a result of pressure applied by the tonometer tip. In this study, the modeled cornea had a spherical radius of 7.800 mm, and the tonometer tip had a cylindrical radius of 1.53 mm. This resulted in the maximum displacement of 0.147 mm, and the maximum contact area of 7.354 mm$^2$. The calculation of the contact area, A, as a function of the spherical radius of the cornea, R, and the depth displacement, δ, is shown in equation (2).

$$A(\delta)=\pi(2R\delta+\delta^2) \quad (2)$$

In Goldmann applanation tonometer, the measured IOP, $P_{GAT}$, is a linear function of the reaction force. It also depends on a calibration reaction force F(P), which is compared to the normal cornea $F_{550}(P_0)$, where the 550 refers to the nominal central cornea thickness of 550 μm, and $P_0$ is the nominal IOP. This is shown in equation (3).

$$P_{GAT} = P_0\left(\frac{F(P)}{F_{550}(P_0)}\right) \quad (3)$$

The virtual models were designed in Autodesk Inventor LT 2015 and simulated in Autodesk Simulation Mechanical 2015 (San Rafael, Calif.). Several simulations were executed to determine the sensitivities, to various properties of the cornea, of the IOP measurement performed with the tonometer equipped with an embodiment of the tip that has a curvilinear cornea-contacting surface. These properties included at least corneal rigidity (Young's modulus), central corneal thickness (CCT), central corneal curvature (CCC), and the presence of the film of tear. Each of these were simulated so as to be comparable to results from other studies in this field.

Before performing the measurement, and because the pressure member (~tonometer tip) makes contact with the cornea, a topical anesthetic (such as proxymetacaine) is typically introduced on to the surface of the eye (for instance, in the form of eye drops). During the measurement, the eye is illuminated by blue light (for example, light delivered from a lamp equipped with a blue filter). In the zone of contact between the surface of the cornea and the pressure member, the film of tears (which contains fluorescein and has green-yellowish hue when illuminated with the blue light) is displaced, as a result of the contact, so that the boundary between the flattened and the curved areas of the cornea is readily identifiable. The contact pressure required for flattening is used as a measure of intraocular pressure.

Figure 1B:
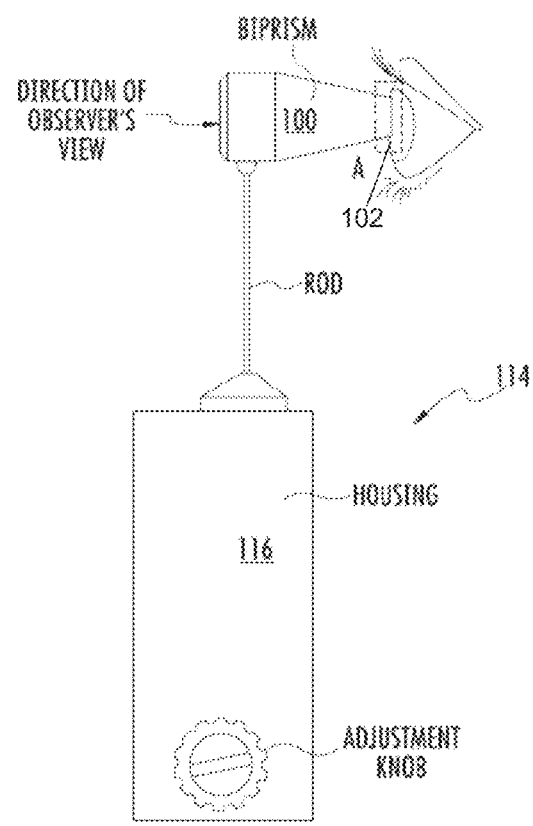
FIG. 1B is a diagram illustrating a Goldmann applanation tonometer of related art employing the tip of FIG. 1B or a tip structure substantially similarly to the tip of FIG. 1.
Figure 2A:
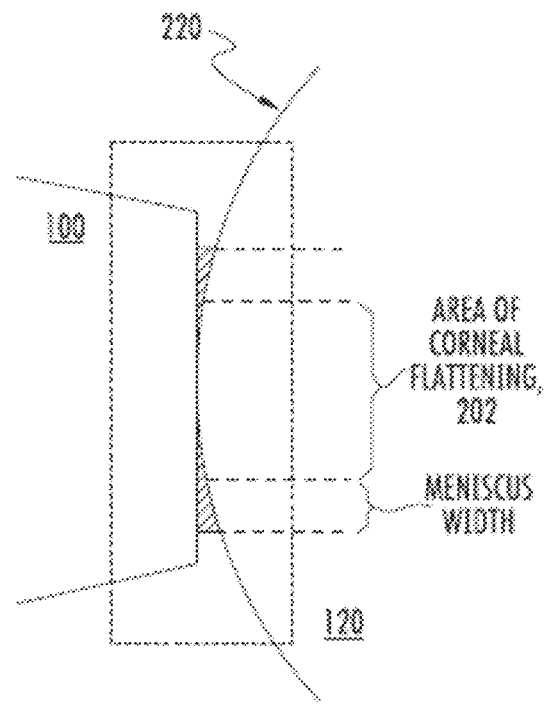
FIG. 2A is a diagram illustrating flattening of the corneal surface due to pressure applied by the tonometer tip.

The classical Goldmann tonometer (see an example 114 in FIG. 1B) has a transparent plastic applanating GAT tip 100 shaped as a truncated cone with a flat surface that is brought in contact with the cornea in operation of the tonometer. The surface of cornea 120 is observed through the plastic applanation tip with the slit-lamp microscope. The device 114 is the most widely used version of the tonometer in current practice of tonometry that utilizes the applanation of the cornea 120. The tip 100 (also referred to as a pressure member, or a corneal contact member) typically contains a bi-prism (a combination of two prisms touching at their apices), which, in reference to FIG. 2A, produces optical doubling of the image of the flattened surface 202 of the cornea 220 and separates the two semicircular image components by a fixed distance or space, across the field of view. Such distance or space is dependent on the apex angles of the prisms. In further reference to FIG. 1B, the Goldmann tonometer corneal contact member or tip 100 is connected by a lever arm to the tonometer body 116. The tonometer body 116 contains a weight that can be varied.

Figure 2B:
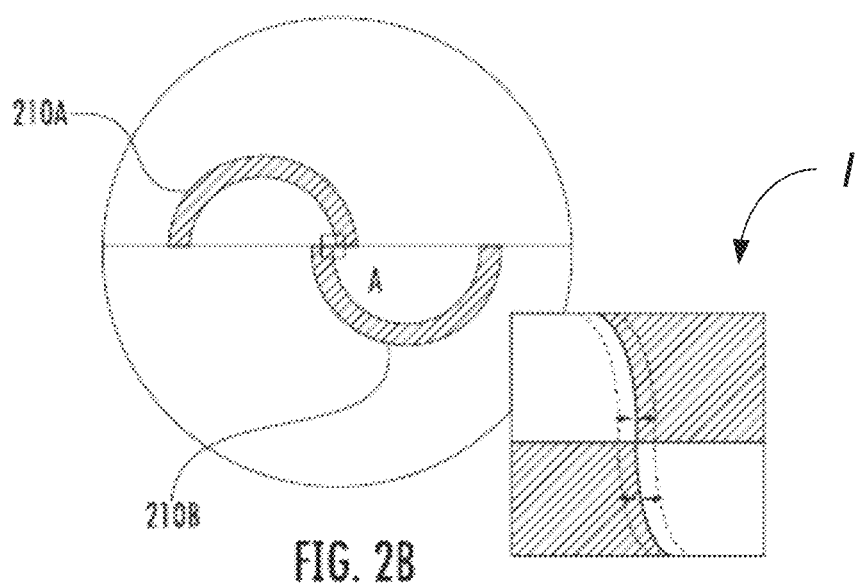
FIG. 2B is a diagram showing the pressure-dependent positioning of two semi-circles representing an image of the flattened portion of the corneal surface.

The observer-examiner uses an optical filter (usually, a cobalt blue filter) to view the two mires (image components shown as semicircles 210A, 210B in FIG. 2B) formed in light propagating through the applanating tonometer (in this case—the tip 100). The force, applied through the tonometer tip 100 to the surface 220 of the cornea 120, 220 along the axis of the tip 100, is then adjusted using a dial (knob) connected to a variable tension spring of the device until the inner edges of the semicircles 210A, 210B, viewed in the viewfinder, are made to meet or coincide (see insert I of FIG. 2B). Such "meeting of the edges" of the mires occurs when a corneal area of about 3.06 mm in diameter has been flattened and when the two opposing, counteracting forces (the first produced by the resistance of the rigid cornea and the second produced by the tension of the tear film) become substantially equal and cancel each other out, thereby allowing the pressure in the eye to be determined from the force applied to the cornea. Notably, as a skilled artisan will readily appreciate, due to the optics of image formation through the flat cornea-contacting surface, the mires are formed and the meeting of the edges (that is, adjacent to one another ends) of the mires can be achieved in the image (as shown in insert I of FIG. 2B) regardless of whether the flat surface of the tonometer tip 100 is centered (co-incident) with respect to the axis of the cornea or is not centered with respect to the optical axis. This non-invasive method of determining an intraocular pressure is inherently imprecise.

Examples of Sources of IOP-Measurement Errors.

Applanation tonometry theory assumes the cornea to be an infinitely thin membrane. The corneal rigidity is significantly affected by the geometric properties of corneal thickness and corneal curvature. Variable material properties of the cornea such as Young's and shear moduli of elasticity both significantly affect the applanating force of the cornea.

In particular, some errors, arising during the measurements performed with the use of the GAT, result from the fact that a cornea (unlike the ideal sphere) has non-zero thickness: a thinner than average cornea typically causes in an underestimation of the IOP, while a thicker than average cornea may result in an overestimate of the actual IOP. To counterbalance the non-zero stiffness of the cornea and in order to applanate a portion of the cornea, additional force is required that cannot be counted towards the actual value of IOP. The studies revealed a correlation between the corneal thickness and corneal stiffness. Clearly, then, the non-zero thickness and stiffness of the cornea introduce the errors to the measurements of the IOP. Accordingly, to reduce—the IOP-measurement error, the value of the force applied to the cornea as measured initially has to be corrected in reference to a second measurement of corneal thickness (the latter measurement being performed using a pachymeter). The accuracy of such correction is predicated upon the accuracy of correlation between the thickness and stiffness characteristics of the cornea, which is also inherently inaccurate (due to influence of such variable factors as age of the person, a diameter of the cornea, corneal curvature, and effects produced by various eye diseases).

Additional cause of the measurement error—not addressed to-date in the art—is the contribution of the non-zero corneal curvature. It was theorized that the influence of the corneal curvature on the accuracy of the IOP measurement may be explained by the difference in the volume of the displaced eye-fluid after the area of the cornea is flattened, and/or the difference in the original volume of the eye, or both (Liu and Roberts, Influence of corneal biomechanical properties on intraocular pressure measurement, J. Cataract Refract. Surg., vol. 31, pp. 146-155, January 2005). The effect of the corneal curvature is independent from the intraocular pressure but manifests an important component of the force transferred from the eye-ball to the tonometer tip, with which it is in contact.

Furthermore, by the very fact of "flattening" of a portion of the otherwise non-flat cornea with which the conventional, flat-tip tonometer GAT prism is brought in contact, the conventional "cornea-applanating" procedure of measuring the IOP produces a sort-of "kink" at a corneal surface. This "kink" manifests a corneal area, in which the curvature of the partially-applanated cornea is changing at a very high rate. This "kink" area, understandably, lies in the vicinity of a perimeter of the applanated portion of the cornea and defines the spatial transition between such applanated portion and the still-curved portion of the cornea that is not in contact with the flat tip of the tonometer. Phrased differently, at the "kink" area the value of the second derivative of the function representing the shape of the partially-applanated cornea is very high and the cornea is significantly distorted, which leads to intracorneal stress (causing additional component of fore and pressure applied to the tonometer tip, which component is not related to the IOP and adds an error to the measurement thereof).

Moreover, the hydrostatic-surface-tension-induced adhesion of the tear film, formed at the surface of the eye, to the tonometer tip during the measurement also adds some highly-variable error to the measurement results caused by capillary pressure exerted by a fluid bridge between the cornea and the tip. However, no clinical quantification of IOP error due to this attractive capillary force has been demonstrated or taken into account to-date, to the best of knowledge of the inventors.

Notably, to-date there is no conclusive and consistent data on the magnitude of corneal biomechanical properties and related factors. False IOP readings—the exact amount of required corrections for which remains uncertain—create the risk for misdiagnosis, resulting in missed or delayed detection of ophthalmological diseases. Therefore, a measurement technique and system that increase the precision and accuracy of the IOP results are required. The use of embodiments of the present invention increases the accuracy of the measurement of the IOP (performed, for example, with the use of a Goldmann applanation tonometer), thereby reducing or even eliminating a need in an auxiliary measurement of the corneal thickness and reducing the overall cost of the IOP measurement and increasing the quality of care. Moreover, the use of embodiments of the invention minimizes both the contribution of the corneal curvature to the IOP-measurement procedure and the intraocular stress caused by such procedure on the eye.

Generally, embodiments of the correcting applanation tonometry surface (CATS) tonometer prism, discussed below, are intended to be a substitute to the conventional, flat-surfaced GAT tonometer prism, in operation of the tonometer system. As such, the clinical use of the CATS prism including force to pressure conversion is intended to be unchanged from the GAT prism. The embodiments of the discussed below CATS prism and associated measurement methodologies are configured to measure the same pressure as that measured with the GAT prism for "nominal" corneas. A "nominal" cornea is defined as that with an average corneal thickness, curvature, rigidity, and tear film, and is generally characterized by a radius of curvature at the axial point of about 7.8 mm, a central cornea thickness of about 550 microns, a width of about 11 mm, a p-value of 0.82 that is a measure of ellipsoidal eccentricity, and an average corneal modulus of elasticity of approximately 0.5 to approximately 1.5 MPa.

It is well recognized, however, that approximately 50% of the patient population do not have a "nominal" cornea. The CATS tonometer prism, discussed below, is designed to significantly reduce all of the identified GAT IOP measurement errors due to variability in cornea-related parameters among the patients. All physical measurements, materials, and properties of the CATS prism are substantially identical to those of the typical GAT prism (with the exceptions related to the geometry of the applanating surface of the prism), and the practical use of the CATS tonometer prism is intended within the overall GAT or Perkins measurement armature and is governed by the same practitioner protocol and measurement technique without calculations or increased clinic time.

Notably, in designing the shape of the cornea-contacting surface of the embodiment of the invention, the finite-element method (FEM) modelling was used.

Below, and in reference to FIGS. 3A, 3B, 3C and 5A, 5B, non-limiting specific examples of the tonometer tip, shaped curvilinearly according to the idea of the invention, are discussed. During such discussion, even when the reference is made only to the embodiment of FIGS. 3A, 3B, it is understood that the similar considerations equally apply to the embodiment of FIGS. 5A, 5B.

Actual IOP measurements were carried out with the applanation tonometer system (such as a Goldmann applanation tonometer) to estimate the value of the IOP by applanating the cornea to a specified area.

During the modelling, appropriate assumptions about the physical behavior of cornea tissue were made. The tissue of the cornea is an assembly of cells with complex anatomies and structural properties. In simulation, tissue was analyzed as a continuum with inhomogeneous material properties. For the purposes of this study, the models were assumed to have three variable material properties: (1) cornea substrate elastic modulus, (2) collagen elastic modulus, and (3) relative collagen thickness. These materials were assigned to particular physical entities in a virtual assembly, and optimized to match real-world behavior.

Geometric and constitutive models were selected based on the results of previous studies. The material properties were determined via analyses of finite element simulations. The effects of the various geometric aspects of the cornea were measured and studied in previous studies. Since the published corneal material properties vary widely, the specific properties were chosen to approximate known reactions to GAT diagnostics. The force required for applanation of a nominal cornea was set near 1.6 g. The cornea was allowed to contribute only 30% of this applanation force under normal conditions, with the rest coming from the intra-ocular pressure. The finite element mesh density was set so that the perimeter of the applanation area would be precise to within 30 μm, but with a measurement tolerance of no finer than 0.1 g.

Example I

Figure 3A:
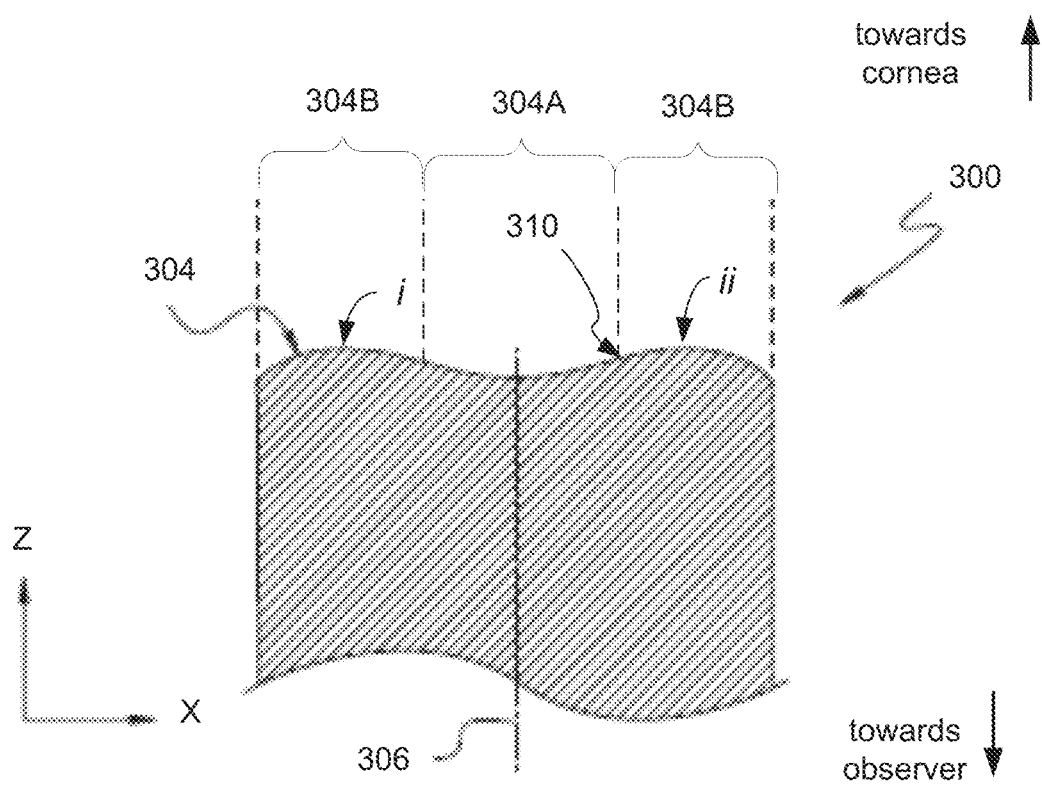
FIGS. 3A and 3B are cross-sectional and top views that illustrate schematically a tonometer tip with a front surface dimensioned according to one embodiment of the invention.
Figure 3B:
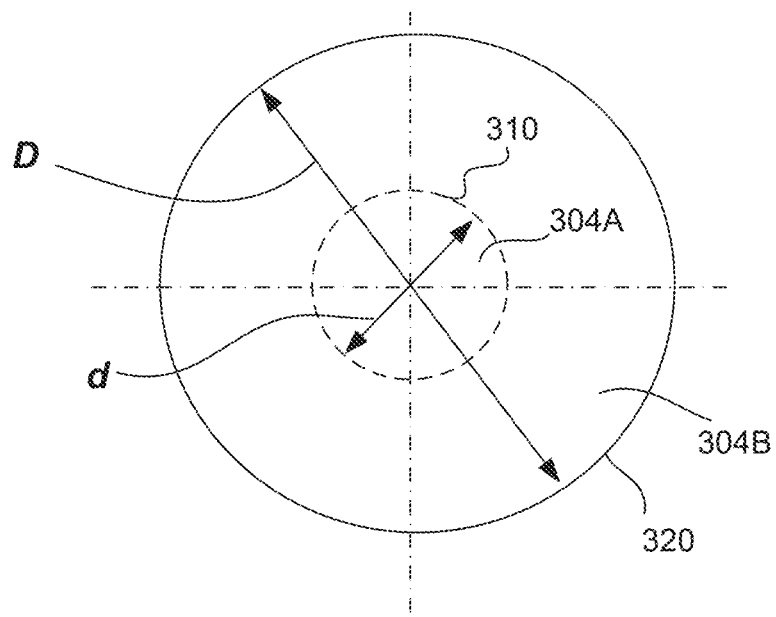

As shown in FIGS. 3A and 3B, a relevant portion 300 representing, for example, a tip of an embodiment of an optical element designed to be brought in contact with the cornea of an eye (and referred to as corneal contact member), is shown in a partial cross-sectional view and a front view, respectively. This embodiment is referred to interchangeably as CATS tonometer tip or CATS tonometer prism. A corneal contact surface 304 includes a central concave surface portion 304A, which in one specific implementation is adapted to with the curvature of the cornea of a typical eye (the radius of which is approximately in the range of 7.8 mm+/−0.38 mm; the typical modulus of elasticity and range of corneal thickness for a cornea of a typical eye is discussed elsewhere in this application).

At a periphery of the corneal contact surface 304, the central concave surface portion 304a passes over into and merges with, in a tangentially-parallel fashion, a peripheral surface portion 304B that has a curvature of an opposite sign (as compared to that of the central surface portion 304A). As shown in the cross-sectional view of FIG. 3A, the surface portion 304B can be characterized as convex. The peripheral surface portion 304B may define a looped (and in the specific depicted case—annular) projection along the axis 306 and onto a plane transverse to the axis 306, and forms an annulus, a ring around the central portion 304A. The central concave surface portion 304A and the peripheral annular portion 304B tangentially and seamlessly merge into each other along a closed curve 310 defined in a plane that is tangential to the surface 304 and that extends transversely to and across the axis 306. Put differently, a first plane (which is tangential to the central surface portion 304A at the boundary 310 between the surface portions 304A, 304B) and a second plane (which is tangential to the peripheral surface portion 304B at the boundary 310 that is shared by the surface portions 304A, 304B) substantially coincide with one another and do not form a dihedral angle. The curvature of the surface 304 at any point along the curve 310 is zero.

In operation, the central concave surface portion 304A may be brought in contact with the corneal surface 220 to applanate the corneal surface across an area contained within the boundary defined by a curve that contains points of maxima of the peripheral portion 304B. As a person of skill will readily appreciate, the largest extend of the portion of the corneal surface that can be applanated (as a result of pressing the surface 304 against the cornea during the measurement of the IOP) without forming a spatial kink in the corneal surface is defined by a substantially axially-symmetric curve that lies in the surface 304 and that includes a plurality of vertex points of the surface 304 (such as vertex points i and ii, as shown in FIG. 3A). (The extent to which the corneal surface can be applanated with the use of a conventional, flat-surfaced tonometer tip 100 understandably does not have such a limit, and the portion of the corneal surface applanated with the flat-surfaced tonometer tip may be substantially as large as the flat cornea-contacting surface of such tip.) Generally, it is not required that the tonometer tip along lateral boundary or perimeter 320 of the surface 304 meet any particular optical, mechanical, or geometrical requirement as this boundary is outside of the contact area with the cornea.

While both the perimeter curve 320 of the front surface 304 of the device 300 and the closed curve 310, along which the central curved surface portion 304A and the peripheral curved surface portion 304B are merging, are shown as circles, it is appreciated that the surface 304 can be configured such as to define at least one of these curves 310, 320 as an general ellipse (defined by the locus of points the sum of distances from which to the two given points is constant). In a specific case, however, the surface 304 is rotationally symmetric about an axis 306. The example of FIGS. 3A and 3B shows just such rotationally symmetric surface 304.

In one implementation, and in further reference to FIGS. 3A, 3B, the concave surface portion 304A includes a spherical surface having a radius of curvature R of e.g. about −9.0 mm (defined in a plane containing the axis 306), and a footprint or normal projection along the axis 306 with a diameter d of e.g. about 3.06 mm (defined in a plane transverse to the axis 306). The peripheral annular (i.e., having a form of a ring) surface portion 304B has a radius of curvature of e.g. about 3.0 mm (defined in a plane containing the axis 306). In such implementation, the footprint or projection of the corneal contact surface 304 onto the plane normal to the axis 306 defines a circle with a diameter D of e.g. about 6.0 mm. The corneal contact surface 304 may be formed in a polymeric material (for example, polycarbonate, with a refractive index on the order of 1.5) or glass with polished finish of optical quality.

Figure 13A:
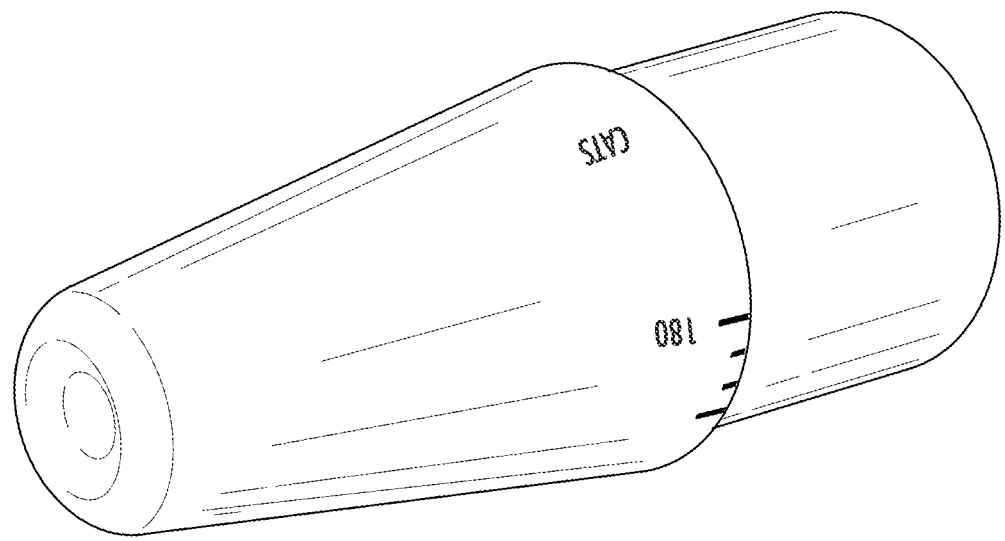
FIGS. 13A, 13B provide schematic illustrations, in perspective views, of an embodiment of the tonometer tip with the applanating surface shaped according to the idea of the invention and an embodiment of the conventional GAT tonometer tip.
Figure 13B:
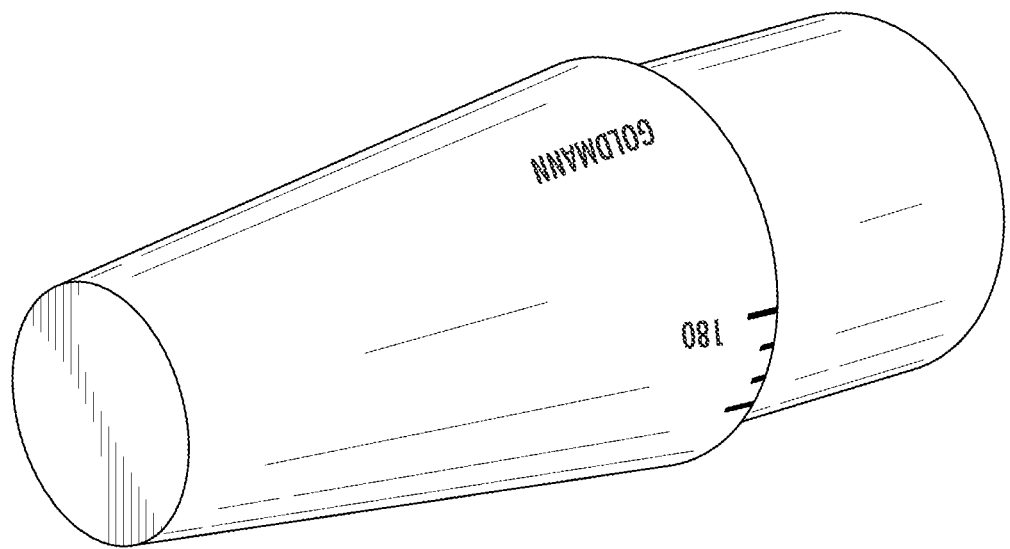

The comparison of renditions of perspective views of the conventional flat tonometer tip (embodiment 100) with that possessing the applanating surface 304 is provided by FIGS. 13B and 13A, respectively.

Figure 13C:
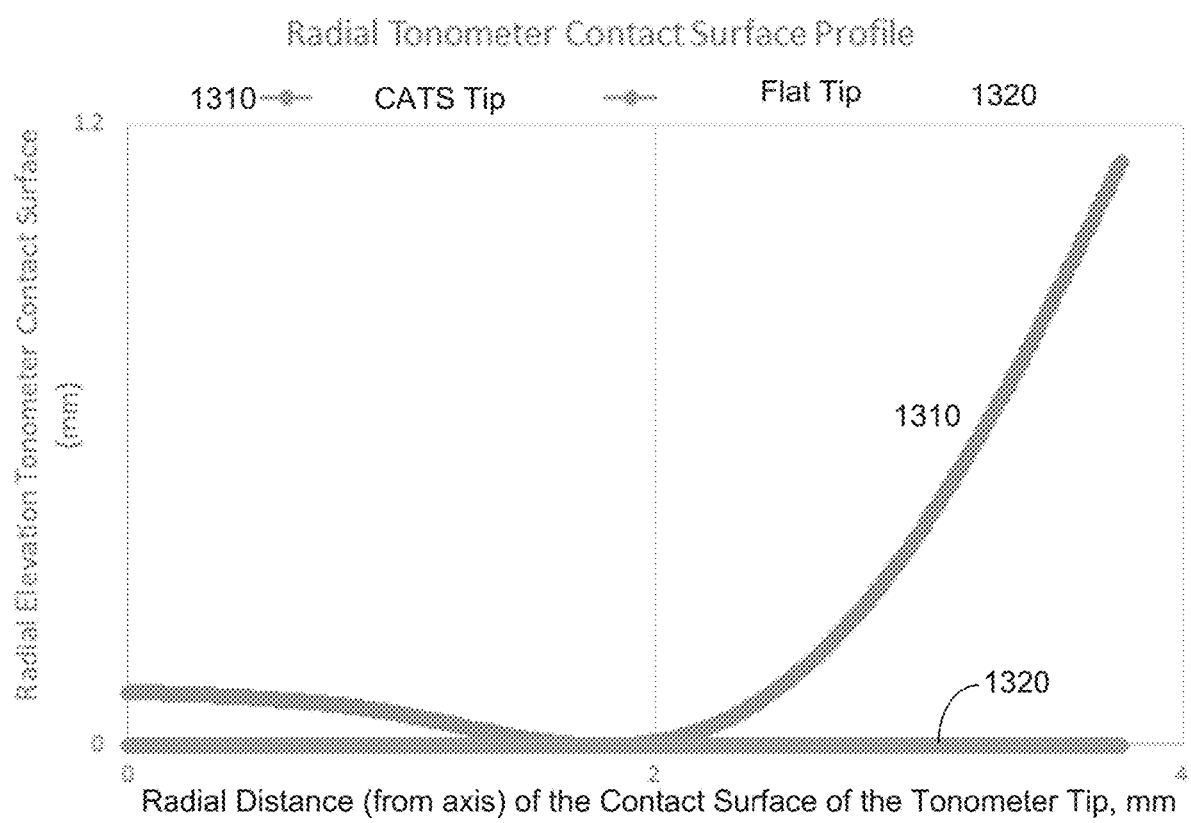
FIG. 13C shows plots, representing a cross-sectional profile of the conventional, flat-surfaced tonometer tip in comparison with that of an embodiment of the invention (the latter sized to reduce contributions of errors, to the results of tonometrical measurements, caused by mechanical characteristics of a cornea and those caused by hydrostatic influence of a film of tear present at the eye during the measurements)
Figure 13D:
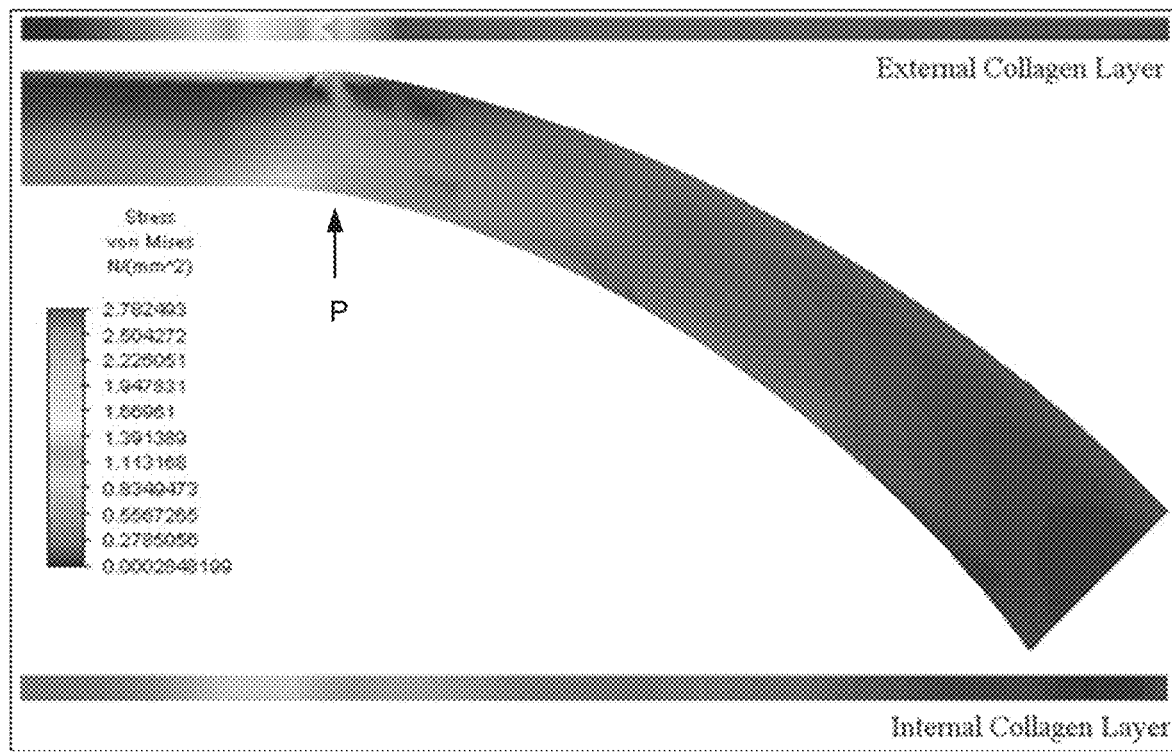
FIGS. 13D, 13E illustrate the distribution of von Mises stress in the cornea applanated with a conventional, flat-surfaces tonometer tip (FIG. 13D) and that in the cornea applanated with a curvilinear tip dimensioned according to an embodiment of the invention, to structurally support the central section of the corneal tissue.
Figure 13E:
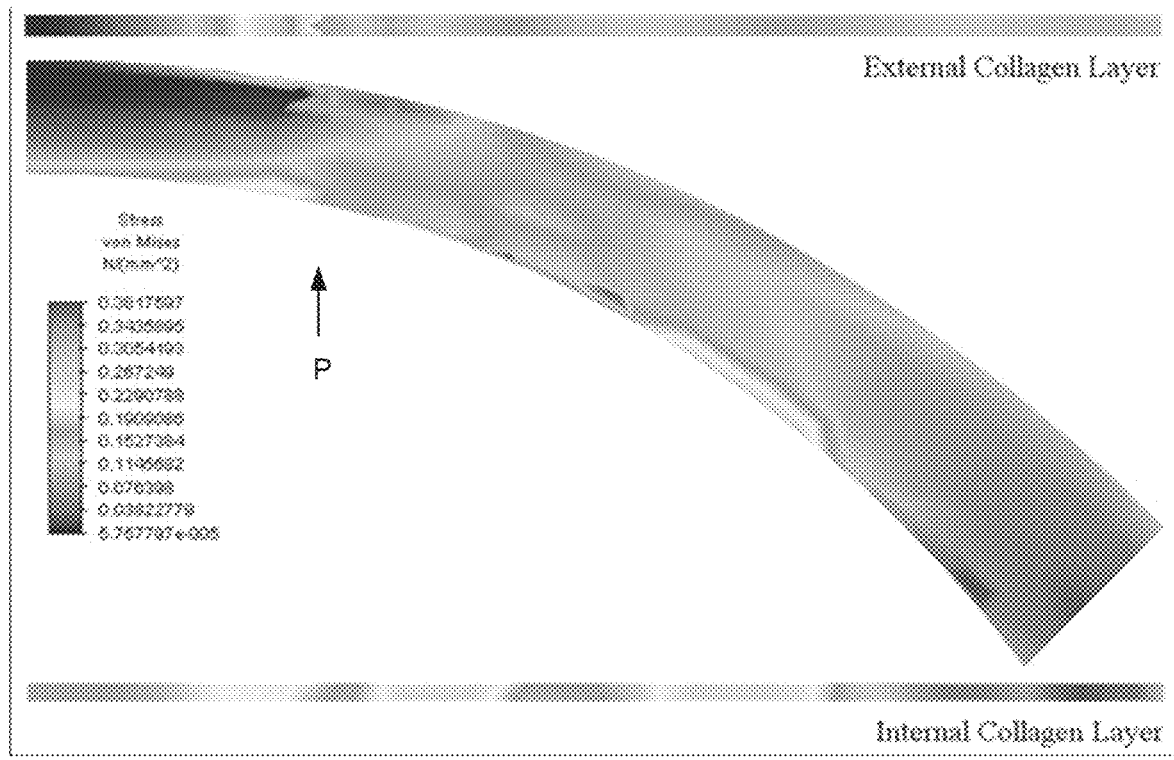

The goal of the design of the curvilinear surface 304, 504, achieved with implementation of embodiment(s) of the invention, was to minimize or at least reduce the intra-corneal stress, formed during the applanation deformation at a location of the cornea (in one case—at a location within the surface of contact between the cornea-contacting surface 304, 504) as compared to the intra-corneal stress that originates during the applanation deformation (at the same location of the cornea) with a conventiona flat-surfaced tonometer tip. In one embodiment, such location is substantially at the perimeter of the tip-to-cornea contact area. (Corresponding to such reduction of intra-ocular stress, the rate of change (the second derivative) of the profile of the corneal surface occurring during the applanation deformation due to the use of the surface 304, 504 is lower than the rate of change of the profile of the corneal surface occurring during the applanation deformation due to the use of the conventional, flat-surfaced tonometer tip.) This translates to the goal of flattening the isobaric curves of the simulated IOP with respect to the error-producing biomechanical parameters such as corneal thickness, corneal rigidity, corneal curvature, and tear film adhesion effects. In one specific implementation, the resulting profile of the CATS tip surface 300 was represented by curve 1310 of FIG. 13C. Von Mises stress for the conventionally-flat tip surface profile and that for the embodiment represented by the curve 1310 are shown in FIGS. 13D and 13E, respectively, as follows: the top bar represents the exterior surface, the bottom bar represents the interior surface, and the center shape represents the sagittal cross-section, demonstrating the substantial reduction of stress figure—up to an order of magnitude or more—when an embodiment of the invention is used (including the perimeter of the applanated area, the location if which is schematically indicated with an arrow P). The embodiment 300 having a cross-sectional profile 1310 yielded a sensitivity (of the measurement) to the central corneal thickness of about 5.0 mmHg/mm, which is a clearly advantageous improvement of about 88.2% as compared with that present when the measurement is conducted with the use of conventional flat-surfaced tip 100, 1320. The curvilinear surface of the embodiment 300, 1310 of the invention reduces the sensitivity of the measurement to the thickness of the cornea by structurally supporting the central section of the tissue, thereby causing the stress, in the cornea, to be more evenly distributed during the measurement. (Compare the results presented in FIGS. 13D, 13E).

Additional advantages of using the curvilinearly-shaped cornea-contacting surface 300 for tonometric measurements are discussed below.

Example II

In an embodiment related to the embodiment 300 of FIGS. 3A, 3B, the corneal contact surface 304 is modified, as compared with the embodiment 300, such as to have different extents in different directions and, generally, a non-axially-symmetric footprint or normal projection. In such a case, the central concave surface portion of the corneal contact surface, while remaining substantially fitted (curvature wise) to the corneal surface, may have unequal extents in two (in a specific case—mutually perpendicular) directions. Accordingly, the peripheral surface portion, while remaining adjoining to the central concave surface portion in a fashion described above, also has a ratio of lateral extents that is similar or even equal to the ratio characterizing the central concave portion.

Figure 3C:
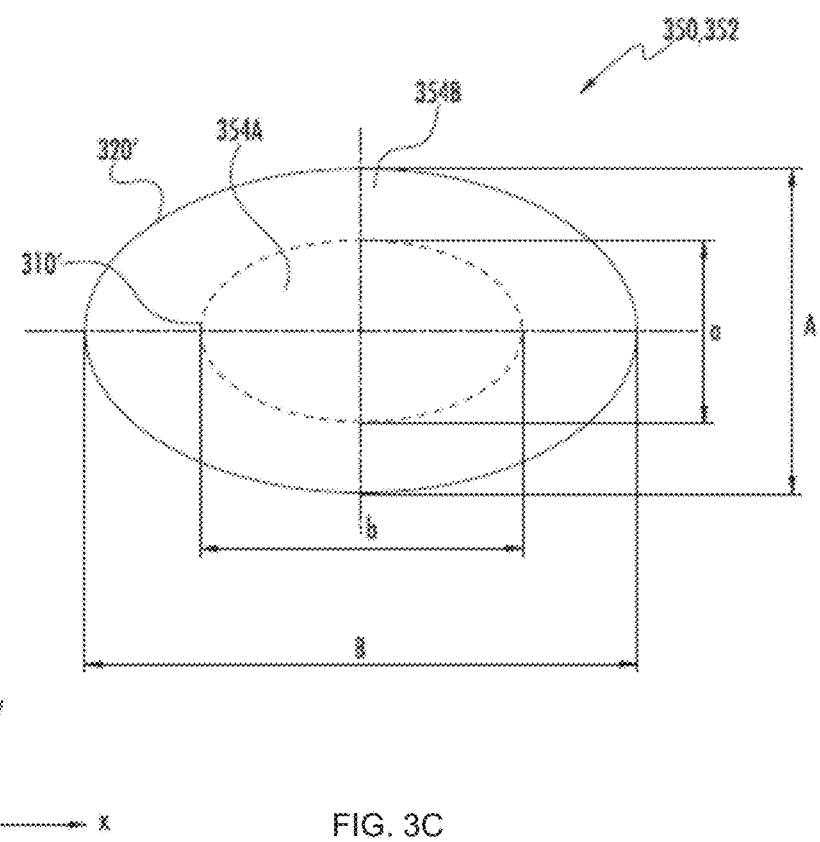
FIG. 3C is a diagram illustrating an alternative embodiment of the invention.

In a specific example shown in top view in FIG. 3C, the so-configured corneal contact surface 350 has footprint 352 defined by an ellipse or oval on a plane that is perpendicular to the z-axis. The surface 350 includes a central, substantially spherical surface portion 354A and a peripheral annular portion 354B, each of which has an elliptically-shaped corresponding projection on the plane that is perpendicular to the axis 306 (which, in FIG. 3C, is parallel to the axis z of the indicated local system of coordinates). As shown, the dimensions of the central surface portion 354A along the minor and major axes of the corresponding footprint are a and b, respectively. The maximum dimensions of the peripheral surface portion 354B along the corresponding minor and major axes of its footprint are A and B, respectively, and indicated by a perimeter 320'. The surface portions 354A, 354B are tangentially, seamlessly merging into one another along an elliptical closed plane curve 310' in a fashion similar to that described in reference to FIGS. 3A and 3B. In this specific example, the corneal contact surface is axially symmetric. In one implementation, a is about 2.13 mm, b is about 3.06 mm. The bi-prismatic element (not shown) that is internal to the corneal contact member having the surface 350 may be oriented such as to approximately bisect the long extent B of the footprint 352 of FIG. 3C.

The implementation illustrated in FIG. 3C is adapted to facilitate the measurements of the IOP of the patients with interpalpebral features that may not necessarily allow the observer-examiner to accommodate a symmetrically-structured corneal contact surface of the embodiment of FIGS. 3A and 3B. It is appreciated that, when the implementation of the invention the operation of which is represented by FIG. 3C is used in practice, the area of the cornea subject to applanation remains substantially the same as that corresponding to the embodiment of FIG. 3B. The lateral dimension of the oval footprint corresponding to 354A that accommodates a narrow interpalpebral fissure (partially closed lids) is reduced, while the orthogonal dimension of the footprint (along the eye lids) is increased, as compared to the diameter of the footprint 304A. Under some conditions, the force required to achieve applanation may be reduced.

Generally, a cornea-contacting surface of the corneal contact member 300 is structured to include an azimuthally symmetric bi-curved surface having a cross-section that is defined (in a plane containing an optical axis of the contact member 300) by an axially-symmetric monotonic curve that has first and second local maxima, one minimum that coincides with the axis of symmetry of such curve. Such axially-symmetric monotonic curve has a second derivative defined at any point of this curve (and is, therefore, fully differentiable within the limits of the curve). Such cornea contact surface includes a central concave portion and a peripheral convex portion that circumscribes the central concave portion. In operation, the central concave portion of the corneal contact surface produces a substantially negligible compression of the central portion of the cornea with which it comes in contact. A region of the corneal contact surface along which the peripheral convex portion and the central contact portion adjoin each other produces a slight corneal compression to define a peripheral ring pattern, observed in form of semicircles, in reflection of light from the cornea.

Figure 3D:
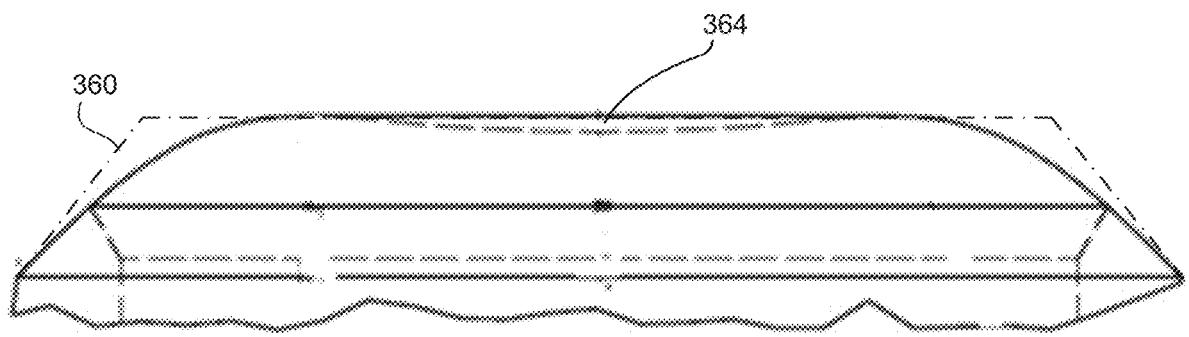
FIG. 3D is an additional illustration of embodiments of FIGS. 3A, and/or 3B, and/or 3C.

FIG. 3D provide an additional illustration, showing the spatial departure of the surface 304, 350, 352, 354 of the embodiment of the CATS tonometer from that of the GAT tonometer tip (illustrated by the dash-dotted line 360) and showing the "sag" 364 of the cornea-contacting surface of the CATS tonometer tip, which is centered at the axis of the tip.

Example III

Figure 5A:
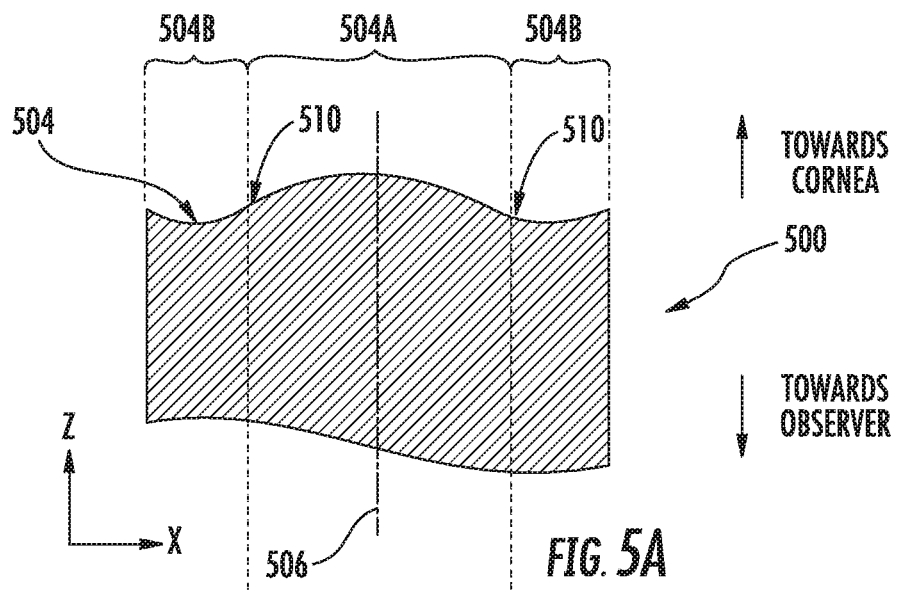
FIGS. 5A and 5B are cross-sectional and top views that illustrate schematically a tonometer tip with a front surface dimensioned according to an alternative embodiment of the invention.
Figure 5B:
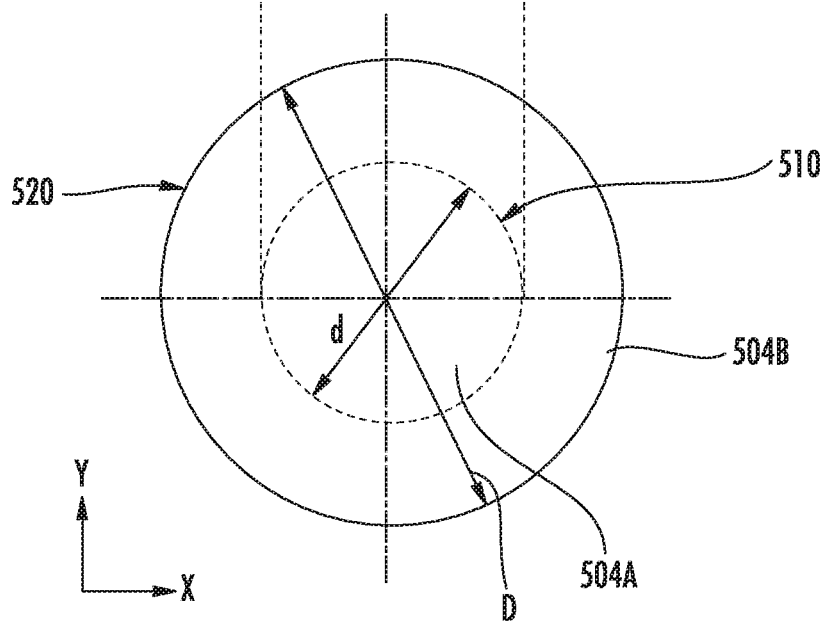

FIGS. 5A, 5B schematically depict a related embodiment 500 of a tip of the corneal contact member shown in a partial cross-sectional view and a front view, respectively. A corneal contact surface 504 includes a central surface portion 504A, the curvature of which has a sign opposite to the sign of the curvature of the cornea. At a periphery of the corneal contact surface 504, the central surface portion 504A passes over into and tangentially merges with a peripheral surface portion 504B that has a curvature of an opposite sign (as compared to that of the central surface portion 504A). As shown in the cross-sectional view of FIG. 5A, the surface portion 504A can be characterized as convex. The peripheral concave surface portion 504B defines a looped (and in the specific case—annular) projection along the axis 506 and onto a plane transverse to the axis 506. The central convex surface portion 504A and the peripheral concave annular portion 504B are tangentially, seamlessly merging into each other along a closed curve 510 defined in a plane that is both tangential to the surface 504 and transverse to the axis 506. Put differently, a first plane (which is tangential to the central surface portion 504A at the boundary 510 between the surface portions 504A, 504B) and a second plane (which is tangential to the peripheral surface portion 504B at the boundary 510 that is shared by the surface portions 504A, 504B) substantially coincide with one another and do not form a dihedral angle. The curvature of the surface 504 at any point along the curve 510 is substantially zero.

In operation, the central convex surface portion 504A is brought in contact with the corneal surface 220. Generally, it is not required that the tonometer tip along lateral boundary or perimeter 520 of the surface 504 meet any particular optical, mechanical, or geometrical requirement as this boundary is outside of the contact area with the cornea.

While both the perimeter curve 520 of the front surface 504 of the device 500 and the closed curve 510, along which the central curved surface portion 504A and the peripheral curved surface portion 504B are merging, are shown as circles, it is appreciated that the surface 504 can be configured such as to define at least one of these curves 510, 520 as an general ellipse. In a specific case, however, the surface 504 is rotationally symmetric about an axis 506. The example of FIGS. 3A and 3B shows just such rotationally symmetric surface 504.

In one implementation, and in further reference to the embodiment of FIGS. 5A, 5B, the convex surface portion 504A includes a spherical surface having a radius of curvature R of about +9.0 mm (defined in a plane containing the axis 506), and a footprint or normal projection along the axis 506 with a diameter d of about 3.06 mm (defined in a plane perpendicular to the axis 506). The peripheral annular (i.e., having a form of a ring) surface portion 504B has a radius of curvature of about 3.0 mm (defined in a plane containing the axis 506). In such implementation, the footprint or projection of the corneal contact surface 504 onto the plane normal to the axis 506 defines a circle with a diameter D of about 3.06 mm. The corneal contact surface 504 may be formed in a polymeric material (for example, polycarbonate, with a refractive index on the order of 1.5) or glass with polished finish of substantially optical quality. A lateral boundary or perimeter 520 of the surface 504 may not be required to meet any particular optical, mechanical, or geometrical requirement as it is outside of the contact area with the cornea.

Figure 6:
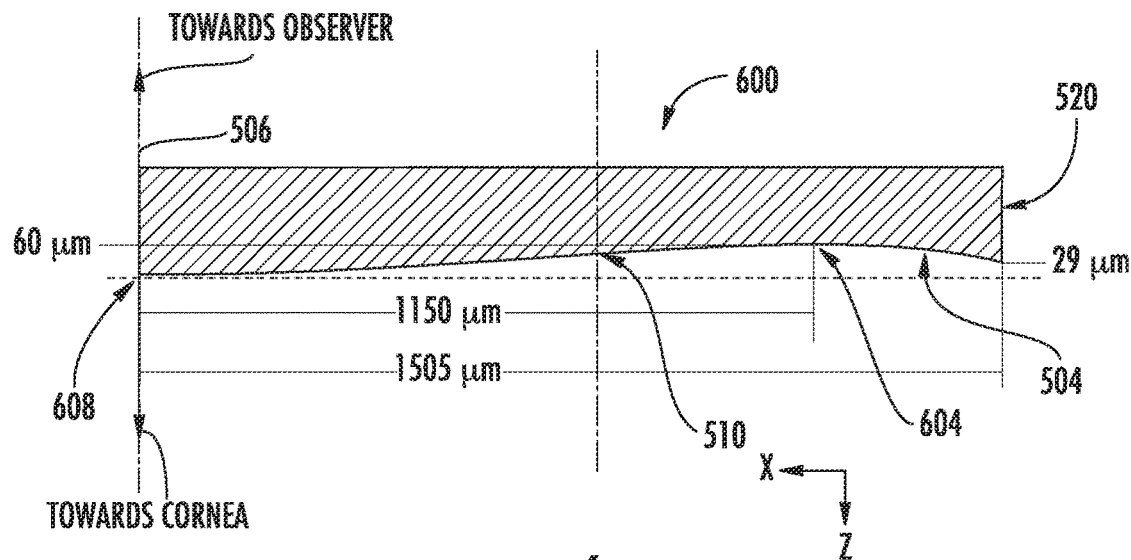
FIG. 6 illustrates a specific embodiment of the front surface of the tonometer tip schematically illustrated in FIGS. 5A, 5B.

A related implementation 600 of the tonometer tip, having a corneal contact surface 504, is schematically shown in a partial cross-sectional view of FIG. 6. As shown, the radius, defined with respect to the 506, at which the annular concave portion 504B reaches its lowest point (an extremum) 604 is 1.15 mm; the axial separation between the apex 608 of the tip 600 and the peripheral edge 510 is 29 microns; the axis separation between the apex 608 of the portion 504A and the bottom 604 of the portion 504B is 60 microns; and the overall radius of the tip, measured in a plane that is perpendicular to the axis 506, is 1.505 mm.

The profile of the surface 504 of the embodiment 600 was determined by optimizing a general surface 504, represented with a polynomial, such as to minimize the second derivative of the profile of the cornea with which the embodiment 600 is brought in forceful contact. The optimization was carried out by minimizing the modulus of the von Mises stress averaged, at a given radius, through the thickness of the cornea.

Figure 7:
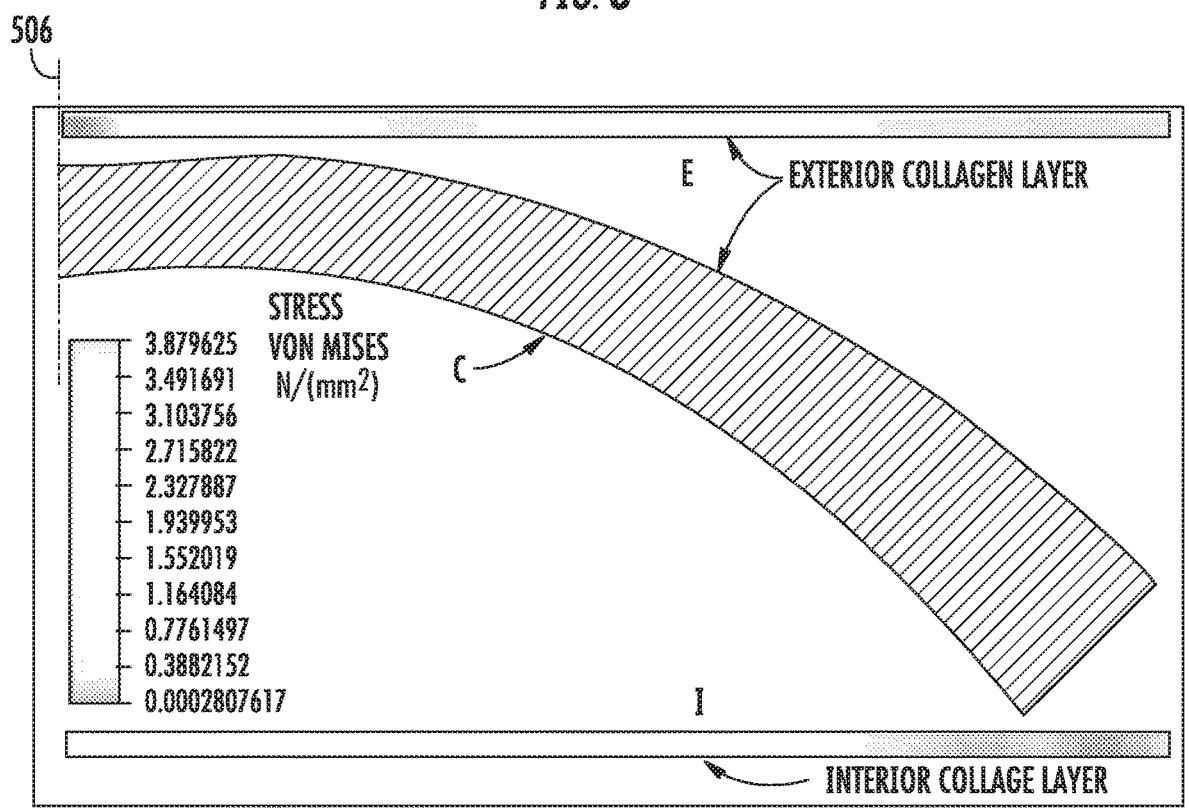
FIG. 7 illustrates von Misses stress in a standard cornea caused by a measurement of the IOP with the embodiment of FIGS. 5A, 5B.

The polynomial optimization of the corneal contact surface 504 of the embodiment 500 was performed with the use of a finite-element method for an average, nominal cornea. FIG. 7 illustrates, in partial cross-sectional view, the average cornea C with indication of spatial distribution of stress formed in the exterior collagen layer E (at the exterior surface of the cornea) and those in the interior collagen layer I (at the interior surface of the cornea). The term "average cornea" refers to a cornea with geometrical and mechanical parameters that are averaged based on known statistical distribution of such cornea parameters across population, i.e. that represented by statistical average of geometric and material properties of human corneas.

Figure 8:
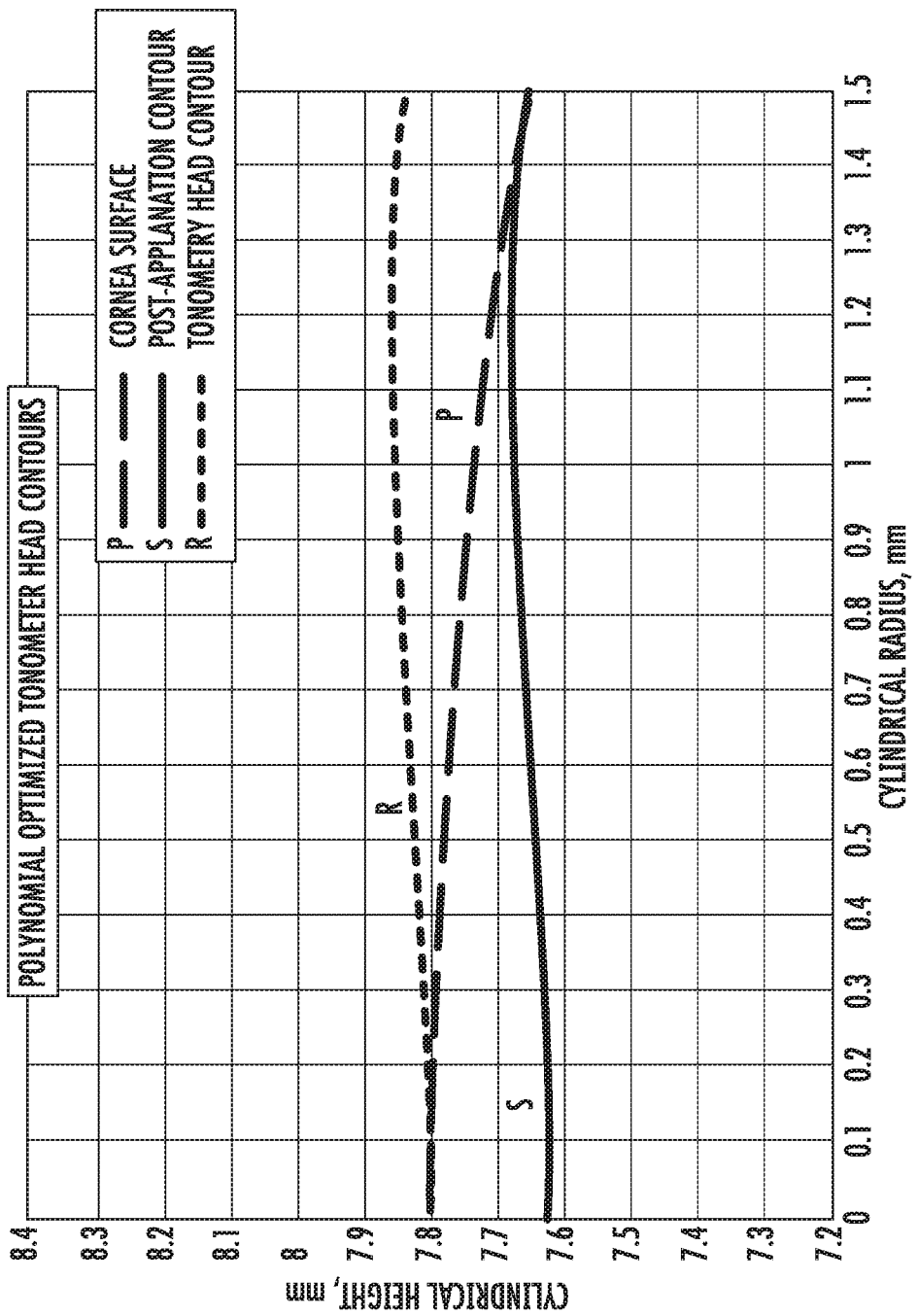
FIG. 8 provides plots illustrating surface profiles of a corneal surface before and after applanation with the embodiment of FIGS. 5A, 5B.

The degree to which the profile of the average, nominal cornea changes when it is brought in contact with the surface 504 of the embodiment 600, illustrated with the use of a polynomial fitting, is shown in FIG. 8 that provides a comparison, on the same spatial scale, the radial profile P of the surface of the free-standing (not in contact with any external tool) cornea, the radial profile R of the surface 504 of the embodiment 600 of the instrument, and the radial profile S of the same cornea post-applanation with the embodiment 600 that is brought in contact with the cornea. The zero value along the y-axis ("cylindrical height") corresponds to the center of corneal curvature.

Example IV

In an embodiment (not shown), the corneal contact surface 504 can be modified such as to have at least one of the perimeter 520 and the curve 510 define a general ellipse. The annular portion 504B could also be shaped to define a corresponding elliptically-shaped ring around the central convex surface portion 504A.

To illustrate the operational advantage of the tonometer tip configured according to an idea of the invention, the shape of the cornea-contacting surface of the tip of the device of the invention can also be assessed within ranges of several parameters that cause the error in measuring the IOP. Among such parameters are a corneal curvature (6-9 mm 95%; 6 mm being a curvature of a very steep cornea), and corneal modulus of elasticity (0.1-0.9 MPa 95%; 0.9 MPa being a modulus of a very rigid cornea), thickness of the cornea (450-700 microns 95%), and thickness of tear film (0-1 mm 95%).

Reduction of a Measurement Error Cause by Corneal Curvature.

Figure 9A:
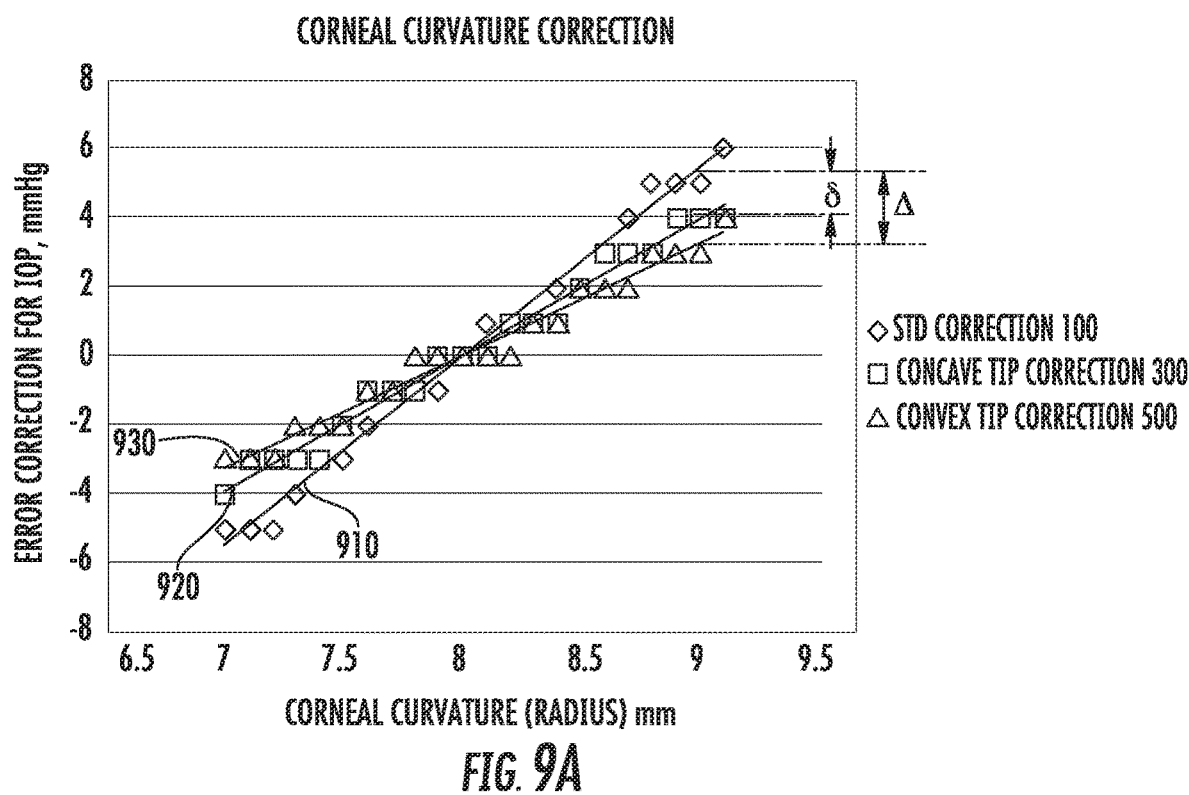
FIG. 9A provides plots illustrating errors caused by the corneal curvature during the measurement of the IOP with a flat-tip tonometer piece, the embodiment of FIGS. 3A, 3B and the embodiment of FIGS. 5A, 5B.

The calculated with the use of the finite-element method (FEM) value of correction for intraocular pressure, required to be taken into account due to the presence of the corneal curvature, is presented in FIG. 9A for each of a conventional flat-tip, GAT corneal contact member 100 (data and linear fit 910), the embodiment 300 of the present invention (data and linear fit 920), and the embodiment 500 of the present invention (data and linear fit 930). The radius of corneal curvature was varied from 6.8 to 9.4 mm, to accommodate empirically known deviations of corneal curvatures from that of an averaged, standard corneal curvature. A skilled artisan would appreciate that the measurements of the IOP carried out with a tonometer tip dimensioned according to an embodiment of the invention (such as the CATS tip 300 or the embodiment 500) imposes smaller intraocular stress on the cornea as compared with those performed with a flat-surface tonometer tip and, consequently, the contribution of error caused by the corneal curvature to the results of the measurement is smaller for the embodiments 300, 500. For example (and considering a particular cornea having a 9 mm radius), the correction to the IOP that has to be introduced to take into account the corneal curvature when the measurement is performed with the embodiment 300 is by $\delta \approx 1$ mmHg or more smaller than the correction required when the flat-tip corneal contact member 100 is used. The use of the embodiment 500 results in an even more precise measurements: here, the error introduced by the corneal curvature is by Δ≈2 mmHg (or even more) smaller that the corresponding error accompanying the measurement with the embodiment 100. Clearly, improving the achievable accuracy of determination of the IOP by about 2 mmHg (out of the standard 16 mmHg of intraocular pressure, or by more than 12%) makes a practical difference in the determination of whether a particular eye has to be operated on. While the influence of the presence of the tear film is expected to somewhat affect the results of the IOP measurements, it was not included in the model.

Figure 20:
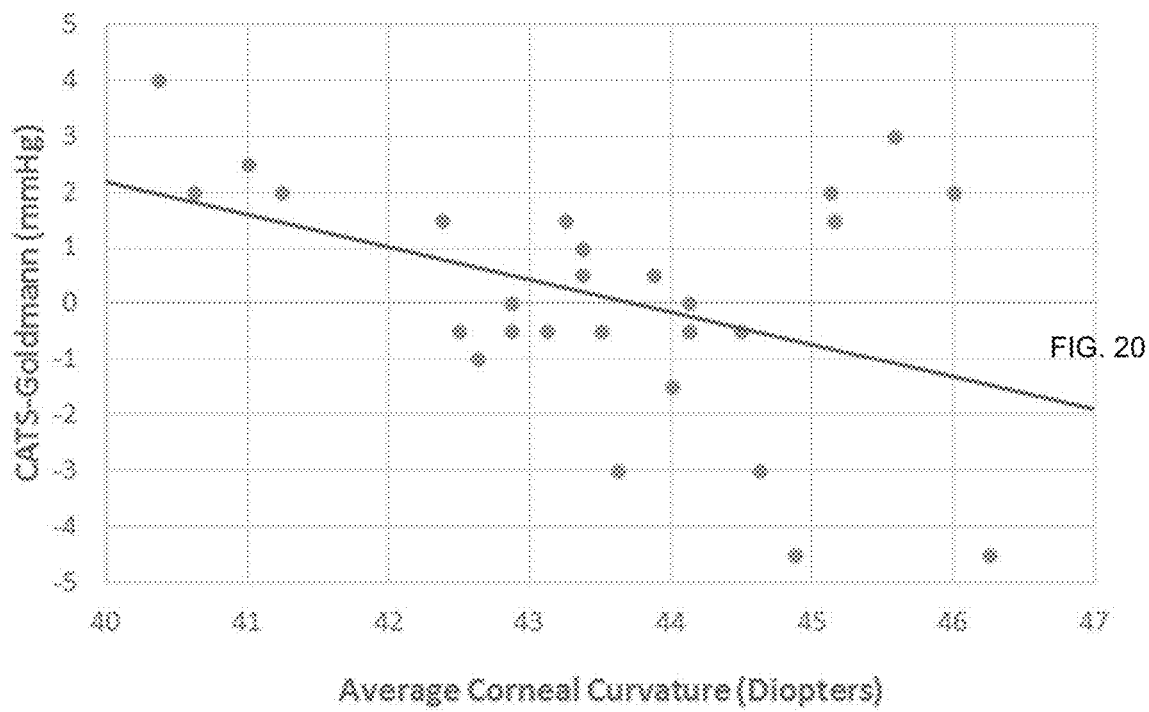
FIG. 20 is a plot showing the difference between IOP values measured with the use of Goldmann applanation tonometer with the use of CATS tonometer tip and those measured with the use of flat-surface, conventional GAT (or Goldman tonometer) tip.

The difference in results obtained with the GAT and CATS tonometer tips was measured and correlated to corneal curvature, see FIG. 20, generally confirming the design theory and that the difference between the results of measurements performed with the use of GAT tonometer tip 100 and the CATS tonometer tip 300 is approximately zero at an average corneal curvature. The average corneal curvature (measured as an average over population and expressed in terms of optical power resulting from the radius of curvature of the cornea, we" understood by a skilled artisan) was 43.6 diopters +/−1.6, standard deviation. These specific data evidences that the use of CATS tonometer tip reduces the IOP error caused by the corneal curvature additionally by +/−2 mmHg (in general—by at least 1 mmHg, modulo value) over the value of error corresponding to the use of the GAT tip at the extremes of the corneal curvature in humans. These finding indicate that the use of the CATS tip substantially corrects the (published in related art) error on GAT of approximately +/−2 mmHg over the range of corneal curvature values. The correlation coefficient associated with corneal curvature error was 0.20.

Reduction of a Measurement Error Caused by Corneal Rigidity.

The curvilinear embodiments of the tonometer tip are also configured to reduce sensitivity of the IOP measurement to the variations of the subjects' corneal moduli of elasticity. Young's modulus or corneal rigidity can vary up to an order of magnitude in individuals and previous studies have demonstrated that this biomechanical parameter of the cornea is age-dependent.

Figure 9B:
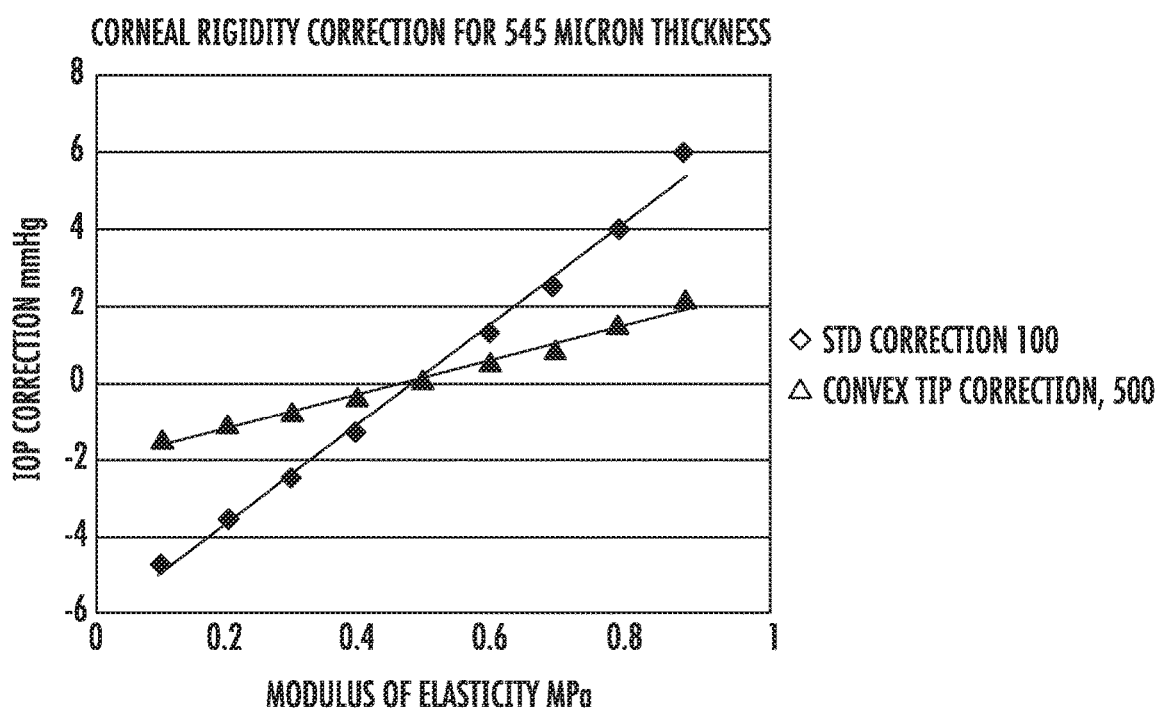
FIG. 9B provides plots illustrating errors caused by the corneal rigidity during the measurement of the IOP with a flat-tip tonometer piece and the embodiment of FIGS. 5A, 5B.

While addressing the influence modulus of elasticity of the composite material of the cornea on the IOP measurement error, on the other hand, the empirically known range of such modulus from about 0.1 MPa to about 0.9 MPa has to be taken into account. FIG. 9B provides plots illustrating that correction to the measured IOP value (required to compensate for the error caused by the corneal rigidity) is substantially reduced when the cornea-contacting surface of the tonometer tip is structured according to the idea of the embodiment 500. The calculations were performed with the FEM for a cornea with thickness of 545 microns (which provides a mid-value for the practically common range of corneal thickness, for a typical cornea, from about 475 microns to about 640 microns). For known individual variations of corneal rigidity, the use of the tonometer tip that is optimized by being configured according to the principles in the examples described above (as compared with the conventional standard of the flat tip) reduces the error by as much as 2 mmHg.

Figure 9C:
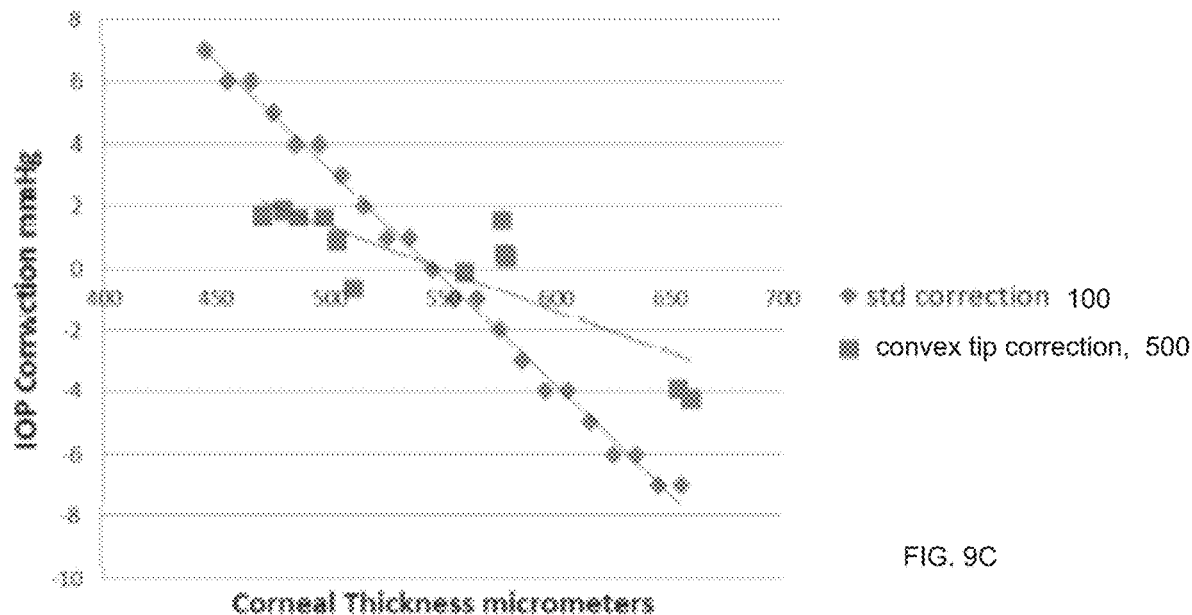
FIG. 9C provides plots illustrating errors caused by non-zero corneal thickness during the measurement of the IOP with a flat-tip tonometer piece and the embodiment of FIGS. 5A, 5B.
Figure 9D:
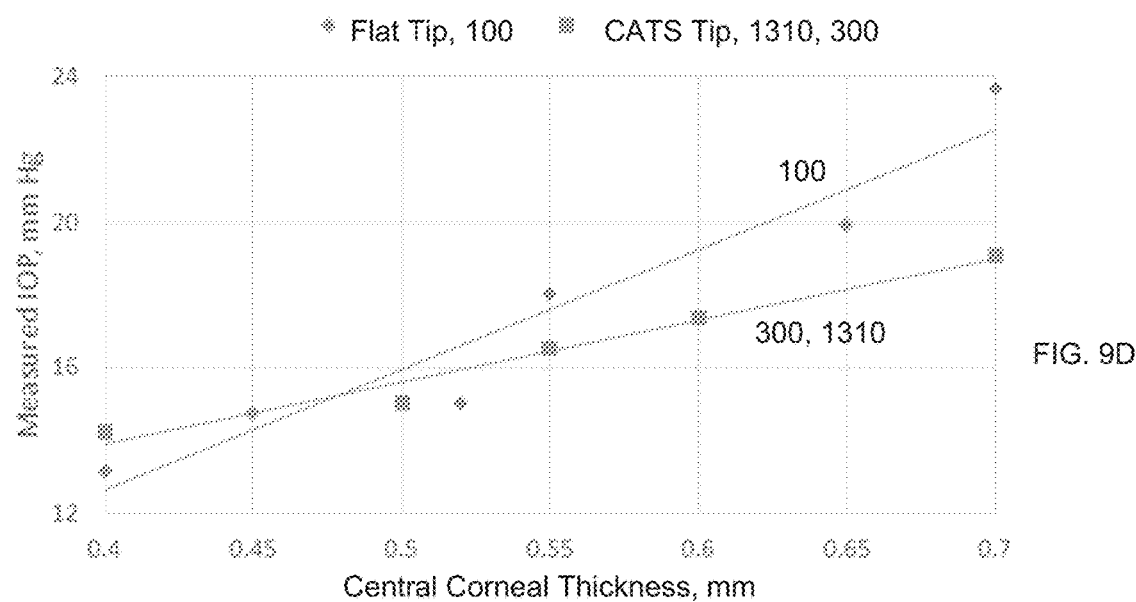
FIG. 9D presents plots illustrating errors caused by non-zero corneal thickness during the measurement of the IOP with a flat-tip tonometer piece and the embodiment of FIGS. 3A, 3B.
Figure 9E:
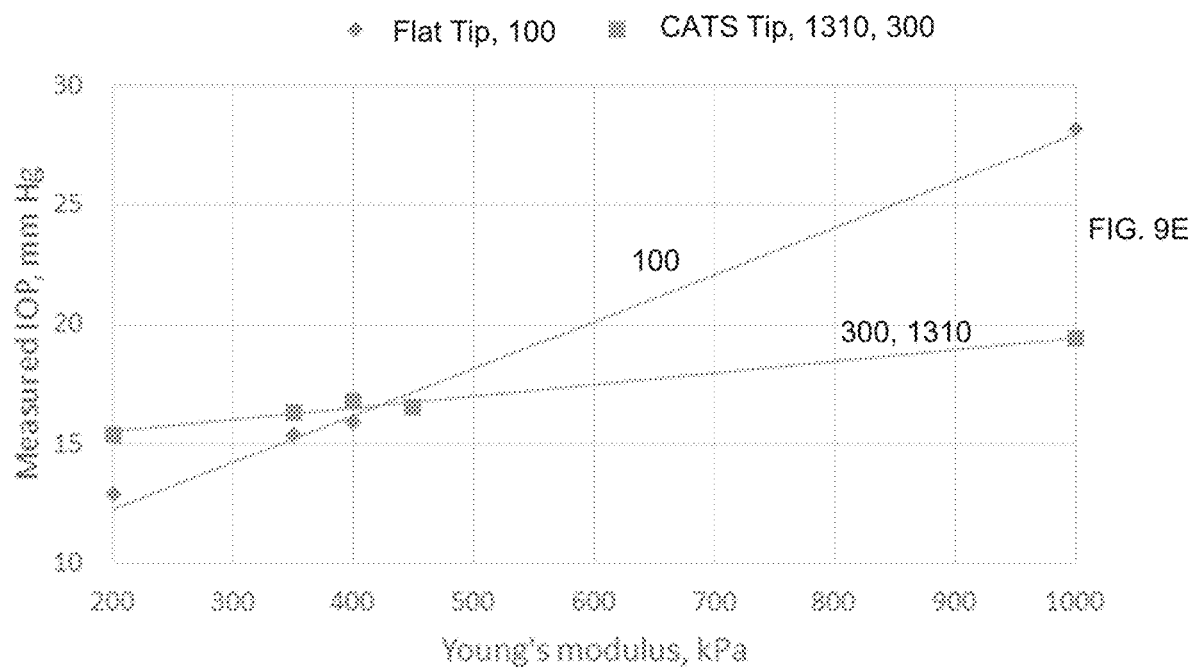
FIG. 9E includes plots illustrating errors caused by corneal rigidity during the measurement of the IOP with a flat-tip tonometer piece and the embodiment of FIGS. 3A, 3B.

The comparison of simulated sensitivities of the IOP measurement to the modulus of elasticity is shown in FIG. 9E for the embodiments 100 and 300. The shallower slope of the curve representing the use of embodiment 300 (as compared with that of the curve representing the use of embodiment 100) indicates that the measurement with the use of the CATS tonometer tip is less sensitive to this source of error. These specific data evidence that the maximum IOP measurement error (caused by variations of the corneal Young's modulus, or corneal rigidity) when using the embodiment 300 is about +/−2 mm Hg, while that assessed for the use of the conventional, flat-surfaced embodiment 100 is about +/−8 mm Hg. In general however, the use of the CATS tonometer tip facilitates the reduction of the measurement error (contributed by the corneal rigidity) by at least 2 mmHg (modulo value), preferably by at least 3 mm Hg (modulo value), and most preferably by at least 6 mm Hg (modulo) value) as compared with the similar measurement error present during the measurement of the IOP with the use of the conventional, flat-surfaced tonometer tip.

A person of skill in the art will readily appreciate that the sensitivity to Young's modulus (corneal rigidity) is somewhat codependent with the central corneal thickness (CCT); the slope of a given plot of FIG. 9E is substantially proportional to the CCT. Therefore, it follows that corneal rigidity (that is, resistance of the cornea to deformation) is dependent upon both the modulus of elasticity and CCT. As is well known, the effects of corneal rigidity on the tonometric measurements of the IOP are typically not corrected for clinically, but could cause more significant error than that caused by the corneal thickness in the measurement of IOP.

Reduction of a Measurement Error Caused by Corneal Thickness.

Plots of FIG. 9C illustrate the results of clinical comparison in vivo of the errors introduced to the IOP measurement by the embodiments 100 and 500 of the tonometer tip. A clear trend could be observed towards substantial reduction of error when the measurement of the IOP is performed with the tonometer tip configured according to the embodiment 500. The practically observed reduction in error, attributed to the non-zero corneal thickness, of up to 2 mmHg—as defined by the use of a tonometer tip configured in accord with the idea(s) of the present invention, and as compared with that during the measurements performed with the conventional flat-surface tonometer tip—is in line with the predictions made by the mathematical model (linear fit).

Additionally, plots of FIG. 9D illustrate the sensitivities of the IOP measurements performed with the use of embodiments 100 and (300, 1310), calculated with the assumptions of the constant values of the Young's modulus and curvature of the cornea and constant IOP. Here, the shallower slope of the linear fit of empirical data representing the results of the measurement performed with the embodiment (300, 1310) and lower values of corresponding variance of the IOP (as compared with those of the curve corresponding to the embodiment 100) are indicative of substantially-improved measurement accuracy. These specific data evidence that the maximum IOP measurement error attributed to the variations in subjects' CCT is about +/−2 mm Hg with the use of the embodiment (300, 1310), as opposed to about +/−5 mmHg in the case of the use of the embodiment 100. Generally, the reduction of the error (attributed to the subjects' CCT) present in the measurement carried out with the use of the CATS tonometer prism—as compared with the error present in the measurement carried out with the use of the flat-surfaced, convention tonometer prism—is at least 1 mmHg (modulo value), preferably at least 2 mmHg (modulo value), and most preferably at least 3 mmHg (modulo value).

Figure 10:
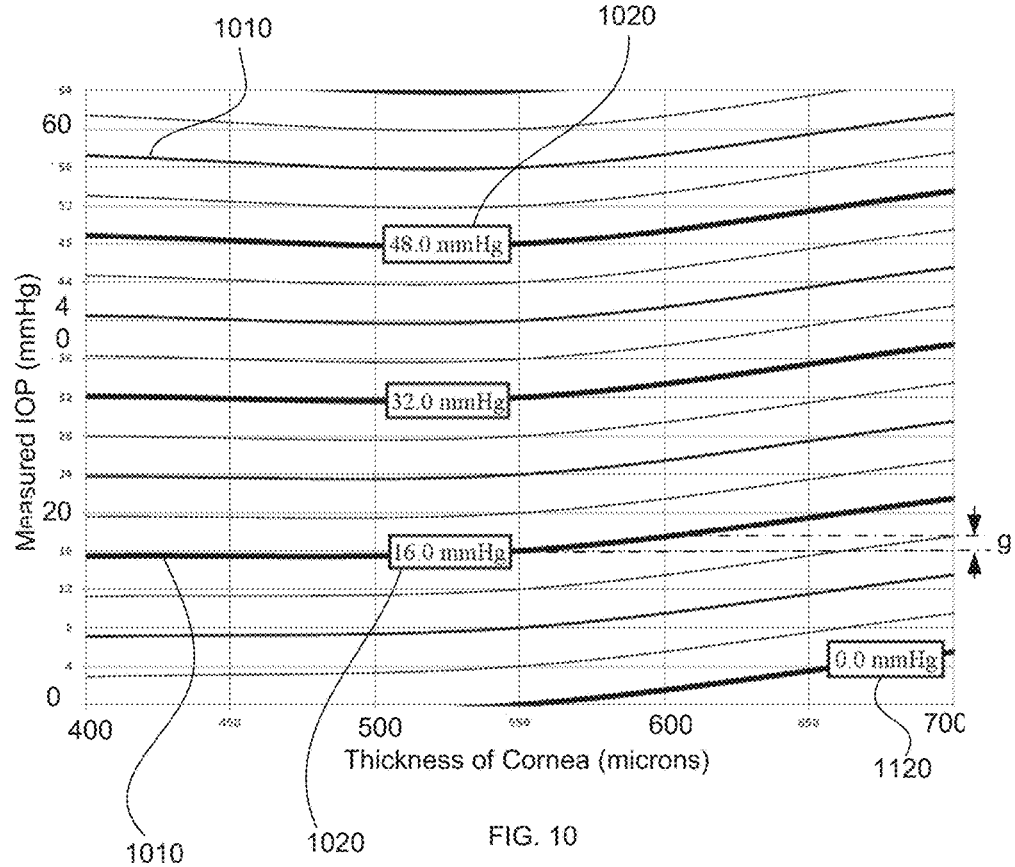
FIG. 10 is a contour plot showing isobaric curves as a function of the corneal thickness for a standard cornea.

FIG. 10, showing the isobaric curves devised with the use of the FEM for the standard cornea, further facilitates the assessment of influence of the thickness of the standard cornea on the value of measured IOP (isobaric curves 1010)

in comparison with the actual IOP (shown as values in blocks 1020). For example, for a typical IOP of about 16 mmHg, the measured value of the IOP will exceed the actual IOP due to the error of about 1.5 mmHg to 2.0 mmHg.

Figure 11A:
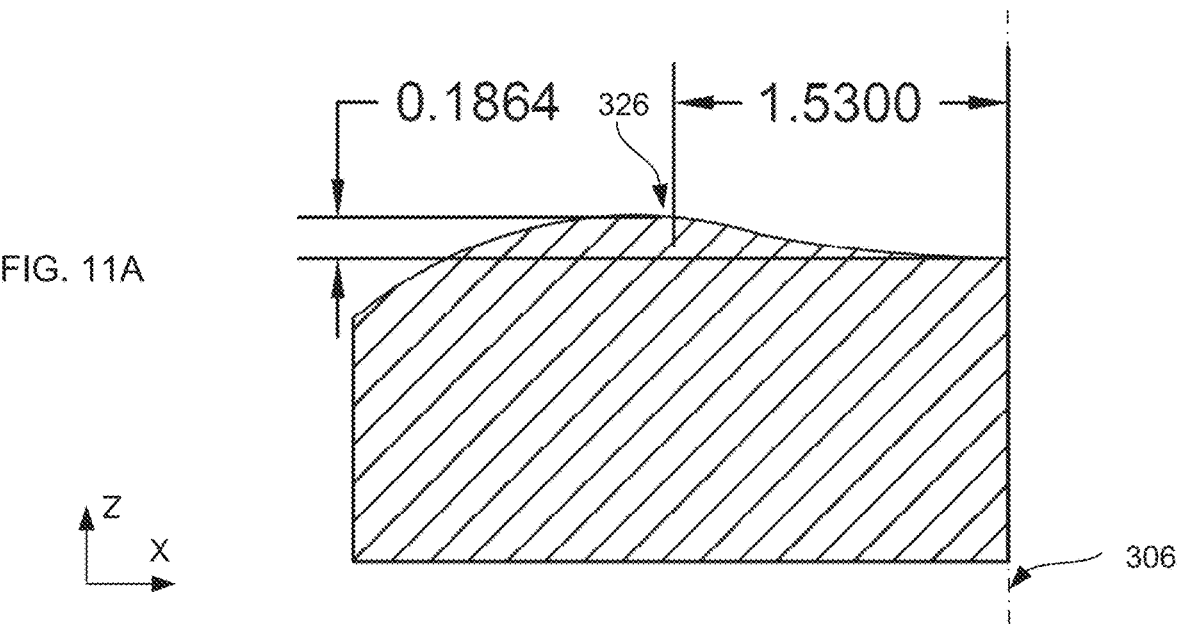
FIGS. 11A and 11B provide specific cross-sectional profiles for embodiments of FIGS. 3A and 5A, respectively.
Figure 11B:
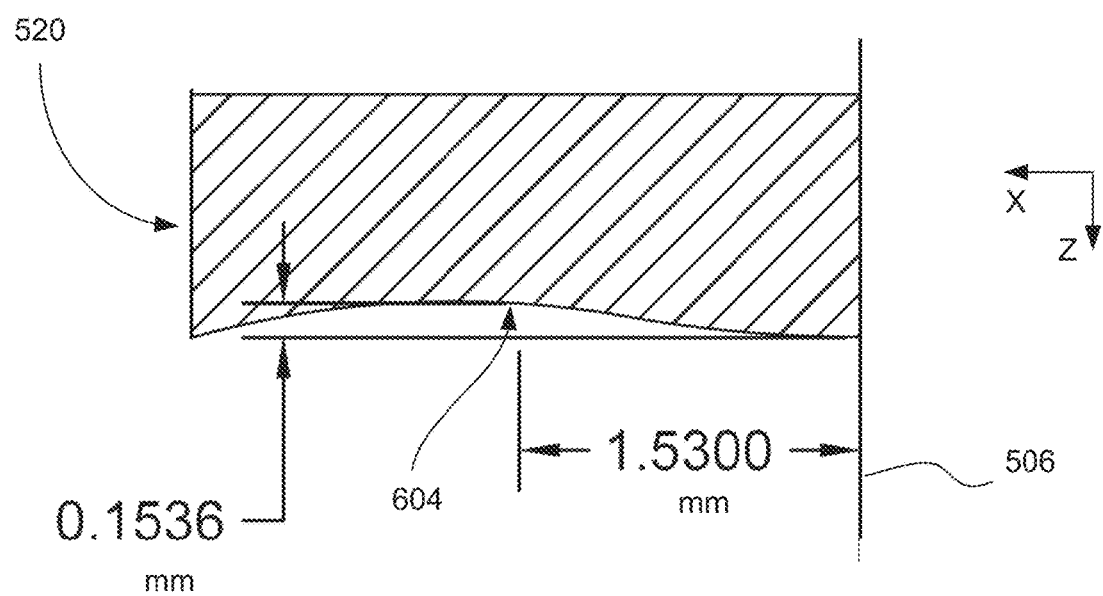

Worth noting is the practical possibility of extreme eye-characteristics that contribute maximally to the measurement error in Goldmann applanation tonometry. Such characteristics include a steep cornea of 6 mm radius, a rigid cornea 0.9 MPa, a cornea with the central thickness of 700 microns, and zero tear film. To this end, FIG. 11A provides parameters of a specific design of the rotationally-symmetric version of surface 304 devised for such extreme situation. As shown, the radius (defined with respect to the axis 306) at which the annular convex portion 304B reaches its top point (an extremum, apex) 326 is 1.53 mm; and the axial separation between the apex of the peripheral portion 304B and the center of the surface 304 (the point of surface 304 at the axis 306) is about 186 microns. Similarly, FIG. 11B provides parameters of a specific design of the surface 504 devised for such extreme situation. Therefore, the judiciously defined curved/non-flat configuration of a cornea-contacting surface of a tonometer tip allows to reduce measurement errors attributed to the biomechanical properties of the eye not only for the typical eye with standard characteristics but also for an eye with rare, extreme characteristics.

Figure 12:
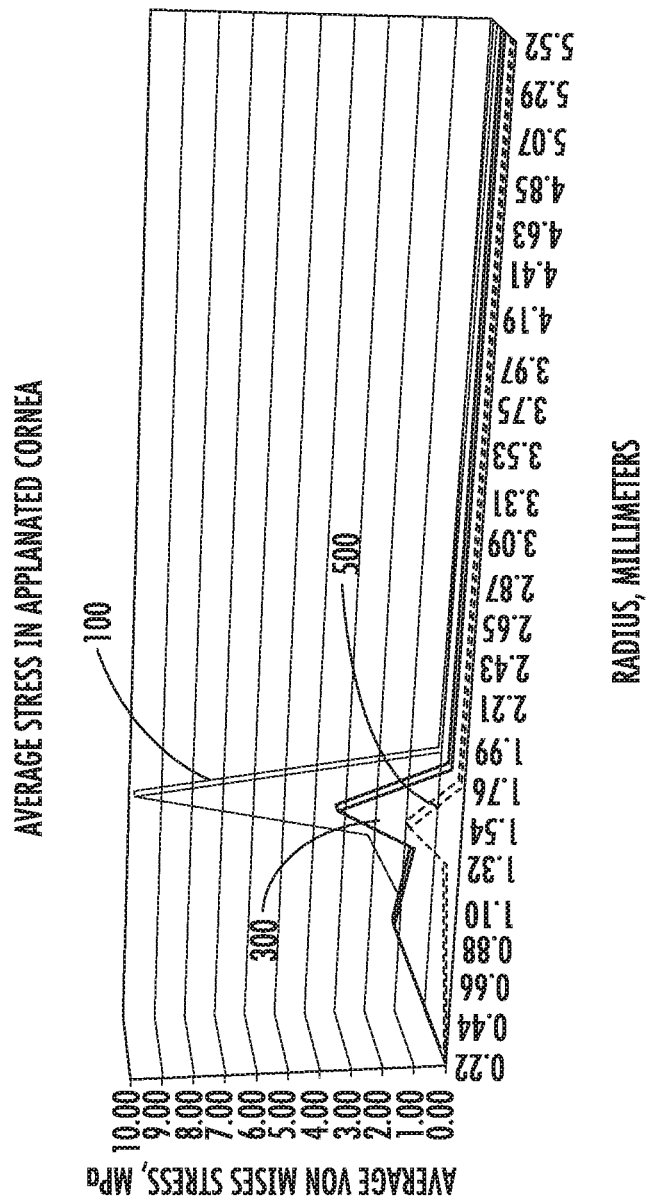
FIG. 12 is a plot showing the reduction of average stress in cornea applanated with a flat-tip tonometer piece, the embodiment of FIGS. 3A, 3B and the embodiment of FIGS. 5A, 5B.

It is appreciated from the above discussion that the key to devising an optimized tonometer tip is minimization of intracorneal stress during the applanating deformation occurring during the IOP measurement. FIG. 12 illustrates additional guidance to advantages provided by the embodiments 300 and 500 of the invention in comparison with the currently used flat-tip standard of the GAT. Shown is the average intracorneal stress (von Mises stress) at a given applanated radial distance from the corneal apex. The use of the tonometer tips dimensioned according to idea of the present invention reduced intraocular stress, and also reduces the second derivative of the deformed corneal surface (or the rate of change of the corneal curvature).

Quantification and Reduction of the Measurement Error Caused by Adhesion of Tear Film (TFE).

While some corneal biomechanical parameters, including corneal rigidity, lead to the over-estimation (or higher measured) of IOP measured with the Goldman applanation tonometry, the effect of the tear-film adhesion partly negates these errors by an effective under-estimation of the results of the applanation IOP measurement. The present study was designed to examine the isolated tear film adhesion error in Goldmann applanation tonometry.

Figures 14A, 14B, 14C:
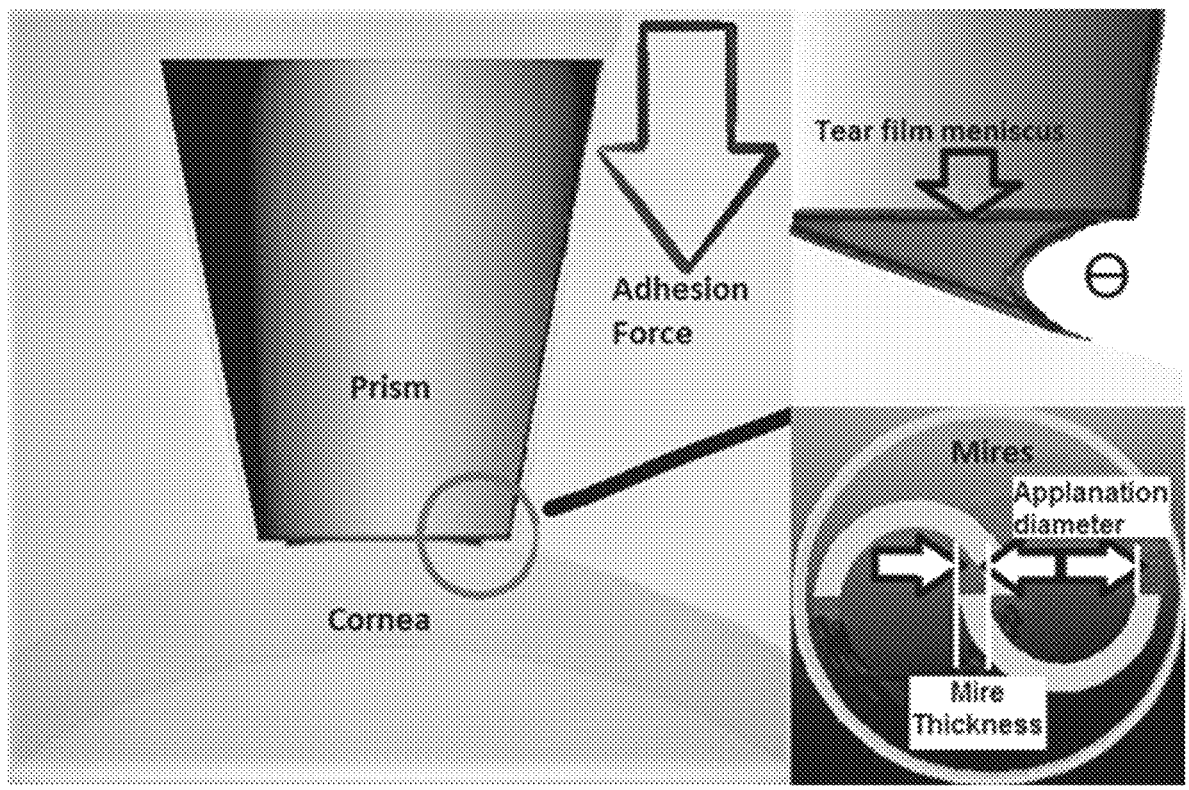
FIGS. 14A, 14B, 14C provide schematic illustration to formation of adhesion (capillary) force caused by the presence of a tear-film in the eye during the tonometric measurements.

FIGS. 14A, 14B, and 14C schematically illustrate the adhesion effect caused by the presence of the tear film during the tonometric measurements of the IOP. The factors affecting tear-film adhesion previously modeled and validated in this study include: i) The contact angle theta ($\theta$) between the tonometer tip and cornea over the tear-film meniscus, FIG. 14B; ii) The linear circumference of the applanating tear-film meniscus, FIG. 14C, and iii) The surface tension of the tear-film.

Figure 14D:
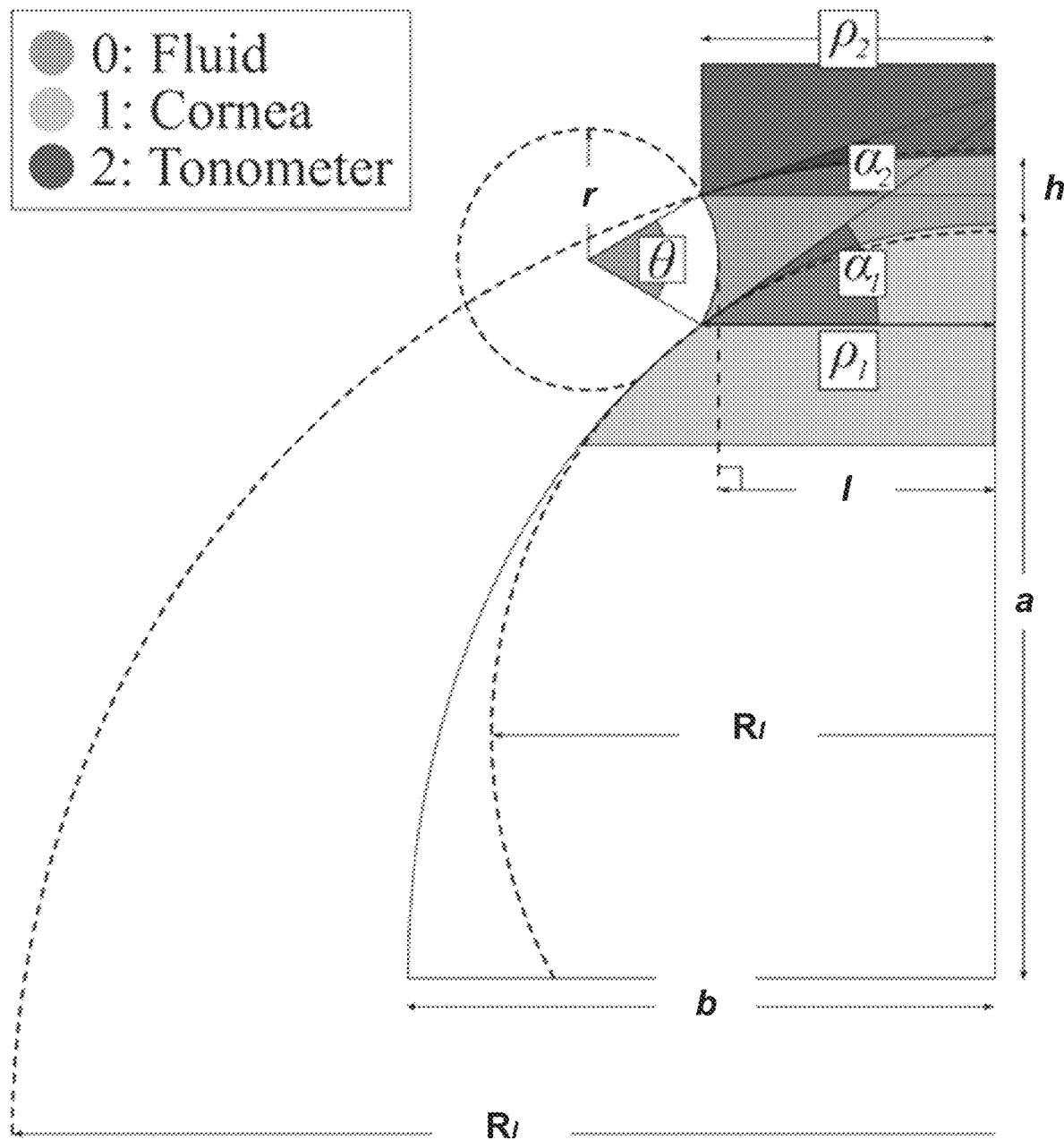
FIG. 14D is a schematic diagram of modelling the tear-film adhesion-caused error.

Mathematical modeling of the situation, carried out with the use of Equation (4), which represents the relationship between the tonometer prism surface and the tear-film of the cornea during full applanation, is schematically illustrated in FIG. 14D.

$$F=\pi*\rho*\sigma*(2*SIN(\alpha+\theta)+SIN(\alpha)*(R/r-R/l)) \quad (4)$$

Figure 14E:
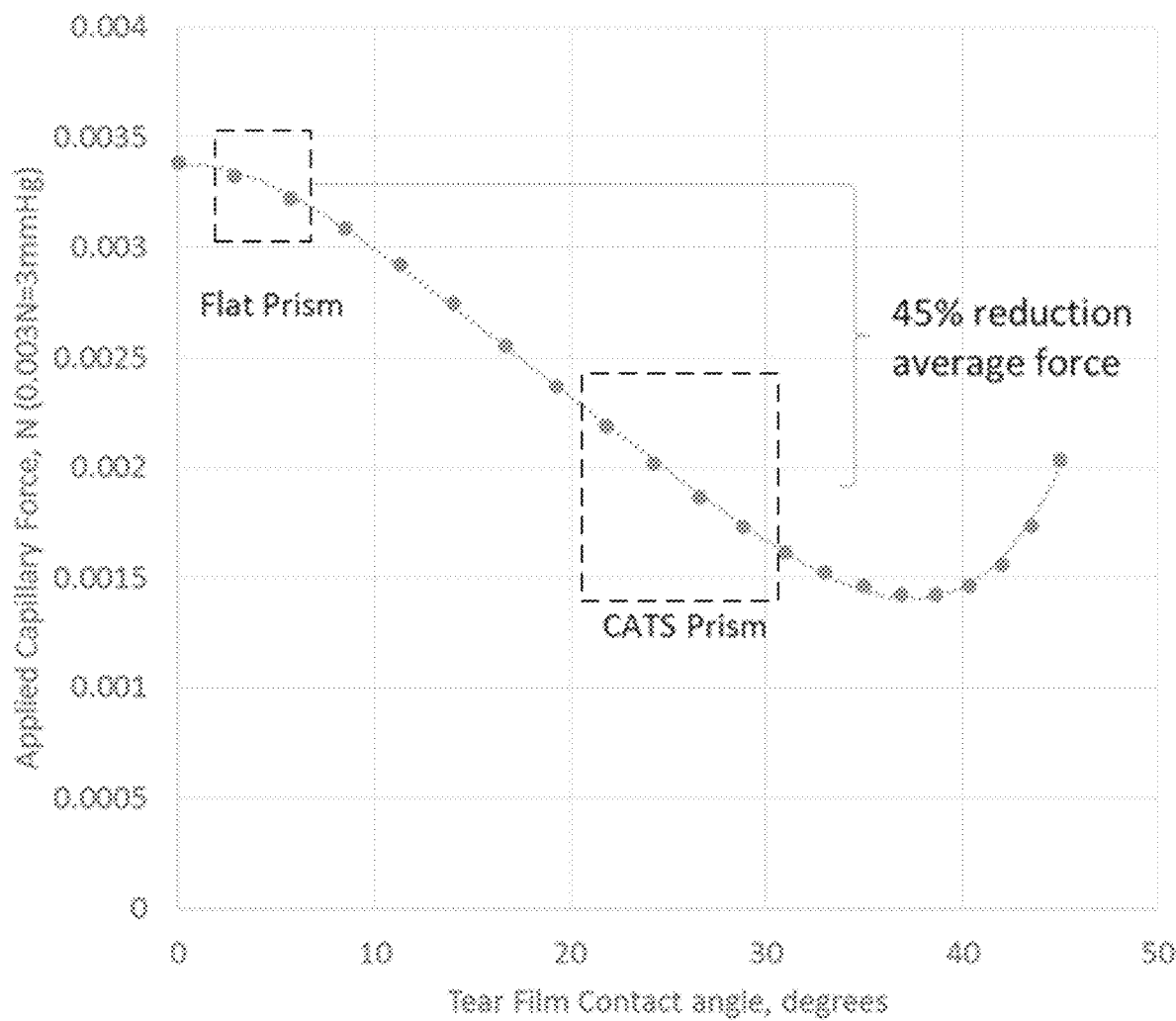
FIG. 14E is a plot representing the corneal tear film adhesion force (0.003N=3 mm Hg)

Here, F=tear film adhesion force (N); $\rho$=Cylindrical radius of contact (mm); $\sigma$=Surface tension (N/mm); $\alpha$=Averaged (over the bridge of fluid) angle between the two solid bodies (rad.); $\theta$=Angle of contact incidence (rad.); R=Effective corneal curvature (mm); r=Radius of curvature of fluid bridge (mm); and l=Radius of fluid bridge (mm). The model predicted an approximate reduction of the TFE as a result of the use of the CATS tonometer tip instead of the GAT tonometer tip, caused by a several-fold increase of the contact angle between the nominal cornea and applanating surface of the tonometer tip from about 5 degrees (in the case of the GAT tonometer tip)—at least twice, more preferably—at least three times, and as shown—to about 25 degrees (in the case of the judicious shaping of the curvilinear cornea-contacting surface of the CATS tonometer tip). To this end, FIG. 14E illustrates the reduction of attractive force, created by the surface tension of the tear film, between the tonometer prism and the cornea as a result of increase of the averaged contact angle between the cornea and contacting prism in the region of the tear film meniscus.

More particularly, based on results of the studies, the TFE was estimated to be between 0.330 grams and 0.415 grams of force in Goldmann applanation tonometry, which translates to a reduced value of the measured IOP (as compared with the true value of the IOP) by about 3.30 mmHg to about 4.15 mmHg.

Empirical quantification of tear-film adhesion force was performed during the tonometric measurements with the use of simulated corneas and cadaver eyes.

In particular, the tear-film adhesion was empirically measured by examining the force required to separate two bodies (that of a tonometer prism and that of a simulated cornea), adhered to one another by an artificial tear-film bridge as illustrated in FIG. 14B. The separation force was measured on a calibrated scale (WeighMax NJ-100, Beijing China) tared between each of the 10 measurements. The tonometer applanation force was reduced at a rate of 0.5 grams/min until prism-corneal separation was achieved. The separation force measured on the scale was recorded at the time of prism contact separation from the corneal surface (simulated acrylic cornea or cadaver cornea).

The tests were conducted using both the CATS and GAT prisms and using both artificial tear solution and fluorescein. Mire thickness measurements were completed only in the fluorescein tests. Ten separate measurements were taken on each of the acrylic simulated corneas and at each manometrically set pressure on each of the cadaver eyes (140 measurements total). The results of each set of 10 measurements were averaged, with indication of a standard deviation. Statistical significance of the results obtained with the use of the acrylic corneas was examined with a general linear mixed effects (GLME) modeling, including variables such as CATS prism, GAT prism, mire thickness, artificial tears, fluorescein, and combined interactions thereof. Statistical significance of the results obtained with the use of cadaver eyes also included IOP (both first and second order IOP effects) and random effects. The difference of the means between groups were examined, as well as the p-value corresponding to a two-sample difference-of-means t-test.

Figure 15:
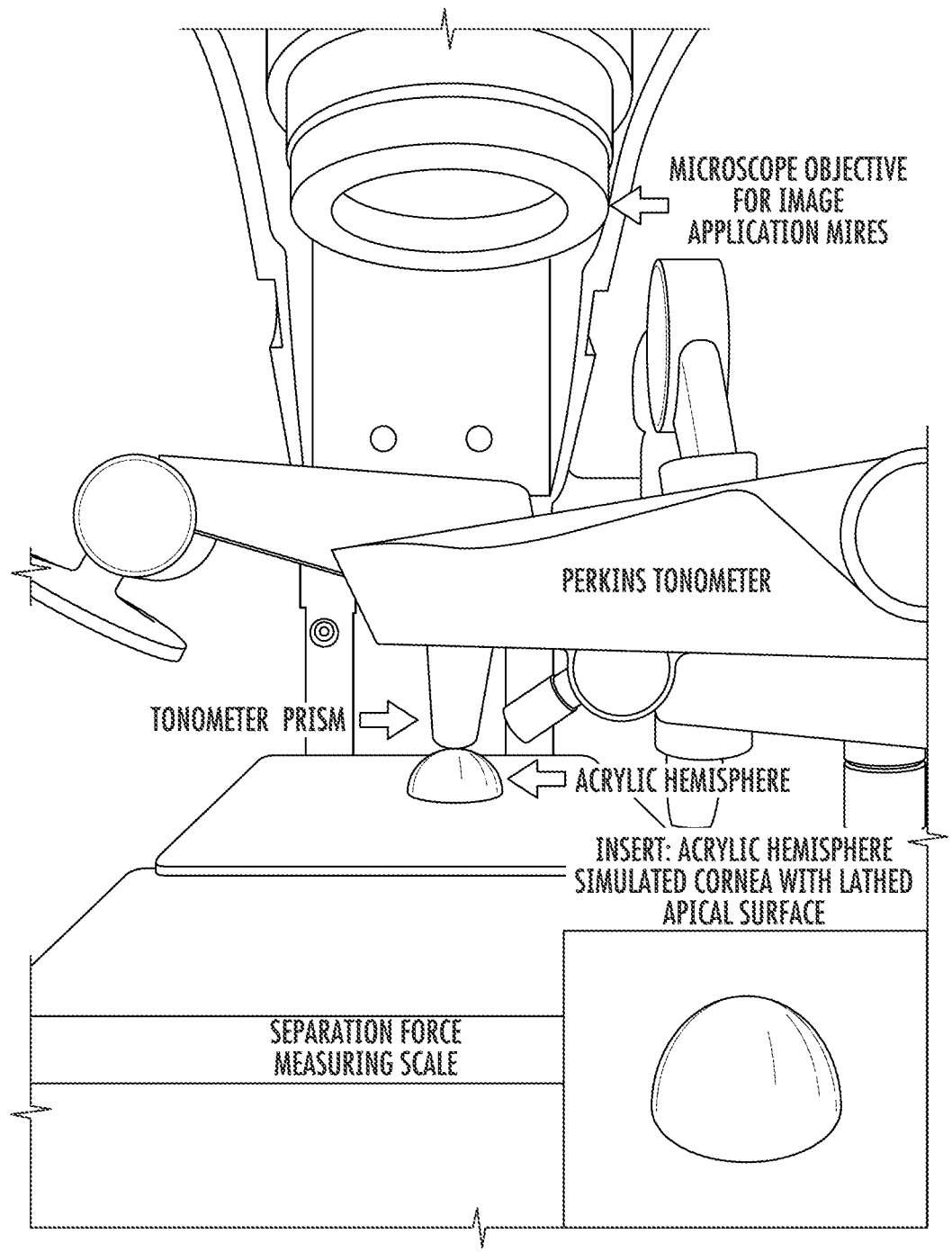
FIG. 15: an image of applanation tonometry tear-film adhesion measurement set-up utilizing a Perkins tonometer, acrylic hemi-sphere as a simulated cornea, scale, and mire imaging microscope.

Test 1: In reference to one set of measurements, involving the acrylic (PMMA) simulated corneas, FIG. 15 presents an image of the test apparatus used for the determination of the PMMA acrylic hemi-sphere adhesion force test. A bench top study was completed using 7.8 mm radius poly-methyl-methacrylate (PMMA) acrylic hemi-spheres 1510 to simulate corneas. The simulated acrylic corneas were lathed flat on their apical surface to a diameter of 3.06 mm for use with the GAT tonometer prism. Simulated corneas were also lathed to the inverse of the CATS prism surface over the applanation area for CATS tear-film separation measurements. This was completed to simulate the isolated tear-film adhesion force at full applanation for each of the GAT and CATS prism. The separation force required for separation of the tonometer prism from the surface of the simulated cornea was recorded at the moment when the simulated acrylic cornea and tonometer prism, connected by a tear-film fluid bridge, were pulled apart.

The applanation mire thickness illustrated in FIG. 14B was measured by imaging mires through a microscope (Amscope12-3, Irvine, Calif.). The microscope image was also used to insure complete and centered applanation between the cornea (both acrylic cornea and cadaver cornea) and the tonometer prism for accurate tear-film separation force measurement.

Figure 16:
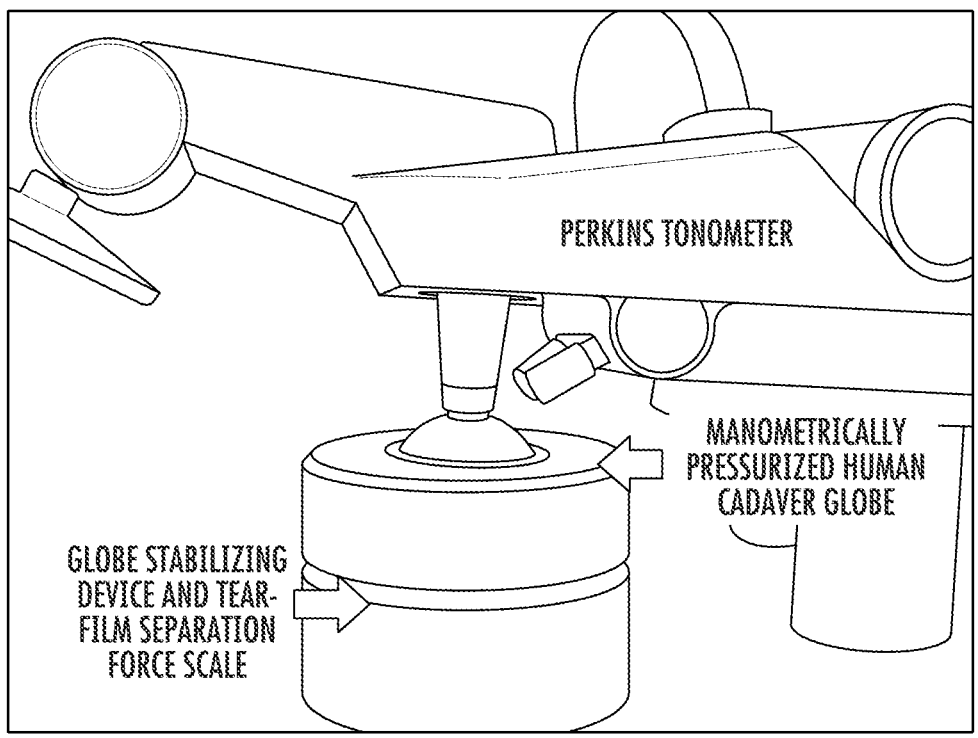
FIG. 16 illustrates an image of an applanation tonometry tear film adhesion measurement set-up with the use of a Perkins tonometer, cadaver eye apparatus.

Test 2: An independent set of tests was completed on two fresh cadaver eyes (Georgia Eye Bank, Atlanta, Ga.). To this end, FIG. 16 presents an image of the apparatus for use with pressurized cadaver eyes, which effectuates a measurement process that is conceptually identical to that utilizing the acrylic simulated corneas. (The whole eye globes were shipped less than 24 hours post-mortem and stored at 4° C. in Optisol chambers until use. All corneas were of corneal transplant quality without prior surgery. The cadaver eyes are used on the day of arrival within 36 hours post-mortem. Eyes with a history or evidence of previous anterior segment intraocular surgery (except cataract) or corneal abnormalities were excluded.) The eye globes 1610 were stabilized in a specially designed apparatus for manometrically pressurizing and measuring IOP on a whole globe with the cornea exposed. A 22-gauge needle with Y-adaptor (Dickinson and Company, Franklin Lakes, N.J.) was then inserted into the anterior chamber via a separate scleral approach. The needle IV tube was connected to a manometric transducer (Dwyer Instruments, Michigan City, Ind.), an isotonic sodium chloride solution infusion bottle, and an open-air reference tube. The IOP was set manometrically to 5, 10, and 20 mmHg, which was confirmed via the pressure transducer. The globe elevation at the central portion of the cornea was maintained equal for all measurements, to ensure a constant intracameral IOP.

Figure 17:
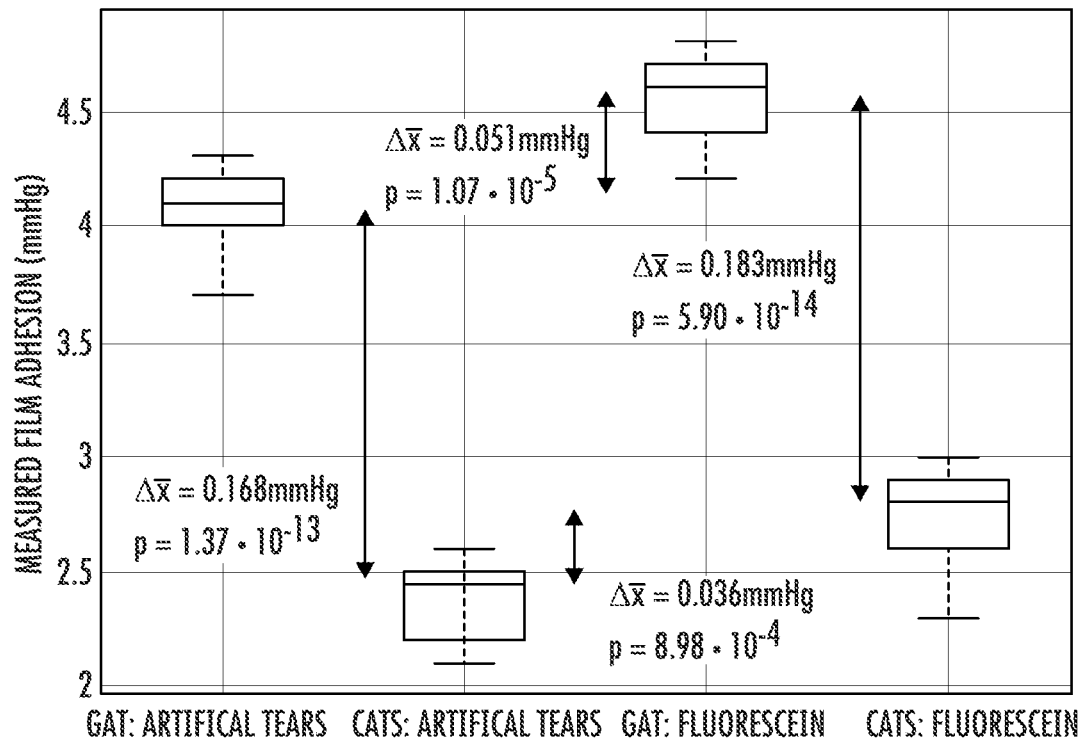
FIG. 17 includes plots illustrating the tear-film adhesion force error (mm Hg) comparison for the tonometric measurements performed with the use of CATS and GAT prisms on PMMA simulated corneas. Box-and-whisker plots are presented for measured film adhesion in cases when artificial tears and fluorescein as tear film simulants were used. The difference between mean values for different groups and the p-value corresponding to a two-sample difference-of-means t-test are also illustrated.

The measurements performed with the GAT tonometer tip demonstrated a significant tear-film adhesion error of 4.57+/−0.18 mmHg at full applanation, when tested using the simulated PMMA hemi-sphere corneas 1510. The TFA error of the measurement performed with the use of the CATS tonometer prism was significantly smaller, at 2.74+/−0.21 mmHg, p<0.001. The difference between the TFA errors obtained with the use of these two prisms is illustrated in FIG. 17.

The data fit, obtained with the use of the Generalized Linear Mixed Effects (GLME) statistical model Ito account t for multiple independent variables) on the cadaver eye data, is expressed by Equation (5) as $$\hat{y}(\text{tear film error}) = 3.28 \text{ [mmHg]} - 1.915 \text{ [mmHg]} \cdot Z - (0.26 - 0.229 \cdot Z) \text{IOP} + 0.0086 \cdot \text{IOP}^2 \quad (5)$$

Figure 18:
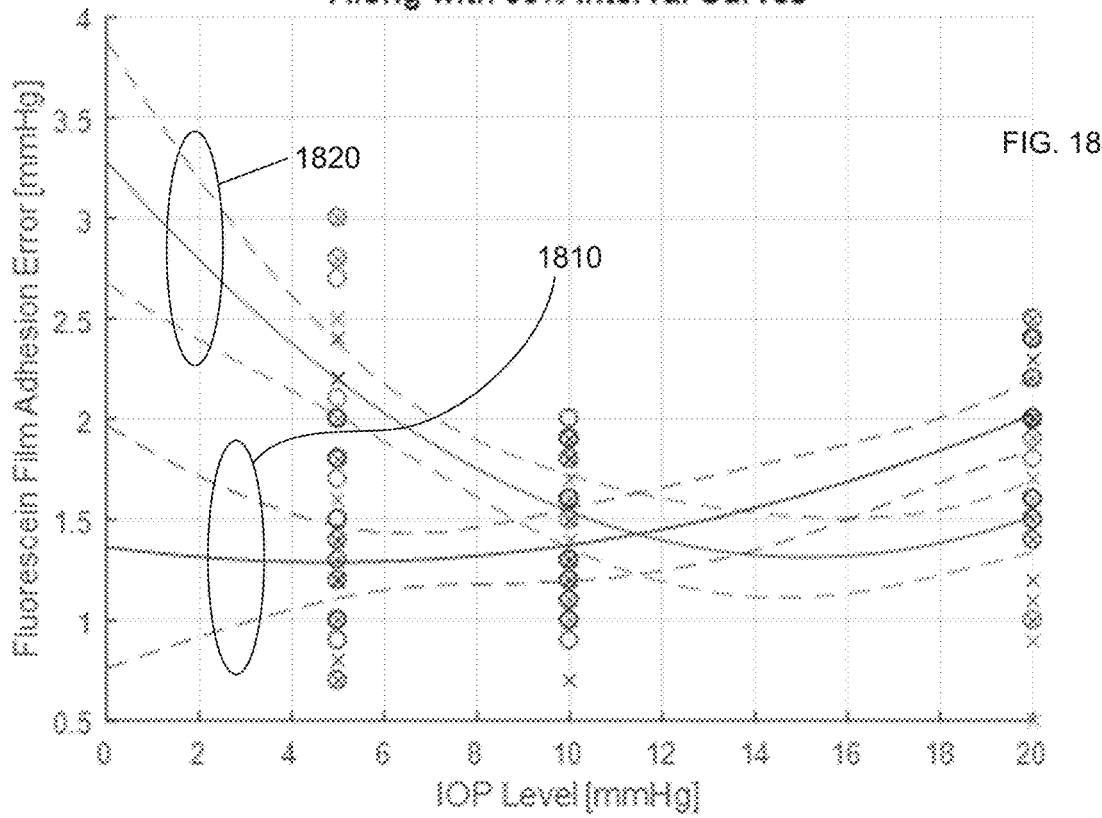
FIG. 18 illustrates cadaver globe tear-film adhesion force error (mm Hg) comparing the data acquired with CATS tonometer tip (curves 1810) and that acquire with GAT tonometer tip (curves 1820) and demonstrating curvilinear fits from GLME analysis along with 95% intervals.

Here, the value of Z correspond to the type of the tonometer tip used in the measurement (Z=0 for GAT tip, Z=1 for CATS tip). The independent validation of the results with the human cadaver eyes 1610, extrapolating the measured tear film adhesion force at zero (0 mmHg) from the 20, 10, and 5 mmHg intracameral IOP separation measurements (FIG. 18), indicated the tear-film adhesion error of 1.40+/−0.51 mmHg present during the measurement conducted with the use of CATS tonometer tip was significantly smaller than that of 3.30+/−0.58 mmHg, p=0.002, present when the measurement was conducted with the use of the GAT tonometer tip.

Figure 19:
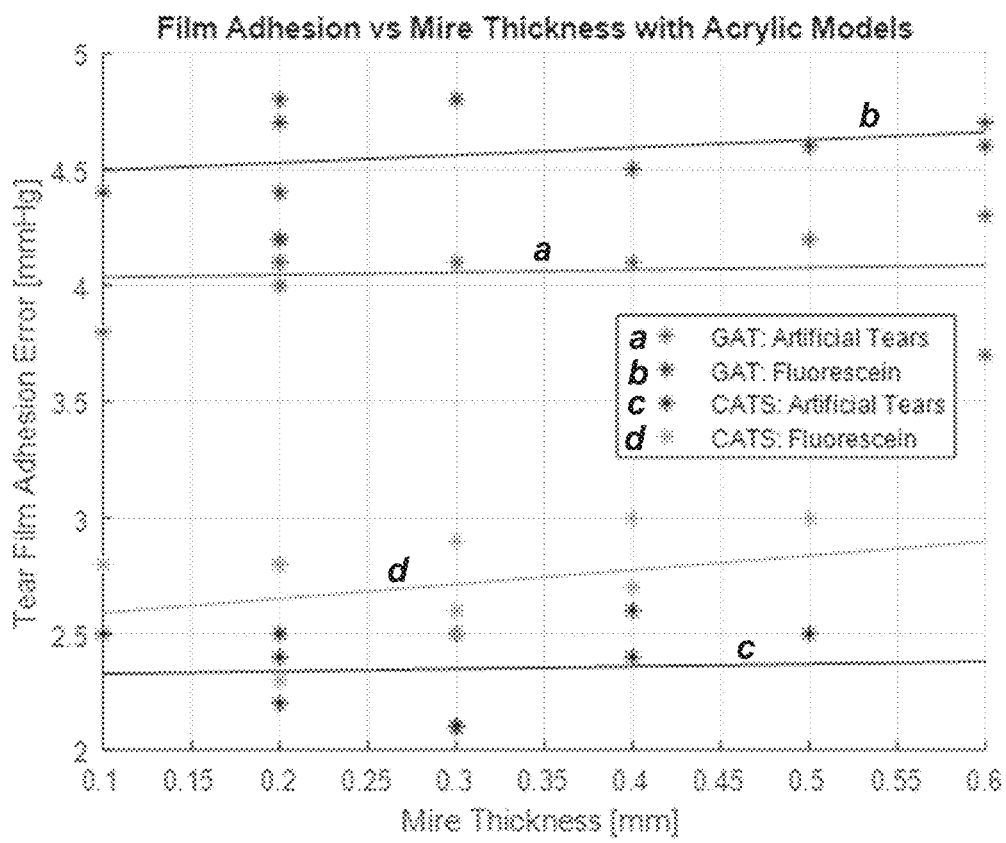
FIG. 19: Tear-film adhesion error versus applanation meniscus mire thickness assessed with the use of CATS and GAT tonometer prisms and GLME multivariate analysis.

The TFE did not appear to correlate significantly with results of applanation mire thickness measurements ($R^2$=0.09, p=0.04). FIG. 19 illustrates that the tear-film adhesion error is substantially independent from the applanation mire thickness (as measured with the use of the PMMA simulated corneas 1510). This independence is in contrast to common teaching about Goldmann applanation technique, which most of related art understands as thick mires can cause an over-estimation in GAT measured IOP. As assessed, fluorescein produces a larger tear-film adhesion error than artificial tears (by 0.51+/−0.38 mmHg, p<0.001, when measured using the PMMA hemi-sphere simulated corneas 1510). The difference between the values of TEF present when using fluorescein from and those when using the simulated tears did not vary significantly in the case of cadaver eyes, 1610, at 0.10+/−0.48 mmHg, p>0.05.

The theoretical and empirical assessment of the TEF, occurring during the applanation-tonometry-based measurements of the IOP showed that the tear-film adhesion force and resulting error in Goldmann applanation tonometry is clinically significant at an IOP underestimation of about 4.57 mmHg. This IOP underestimation value, empirically shown by the testing, is substantially close to the theorized IOP underestimation range of values of 4.1 mmHg and 3.3 mmHg. While the tear-film adhesion is originally thought to negate some of the error caused by corneal rigidity, the multiple error parameters related to corneal rigidity and the tear-film error have considerable variability in individual patients, which leads to clinically significant errors in IOP measurement.

The use of the CATS tonometer prism instead of the GAT prism during the measurement of IOP with the applanation tonometry substantially reduced the tear-film adhesion caused error—by about 41%, in one non-limited embodiment discussed above. Here, the results of empirical testing confirm the results of mathematical modeling, predicting a reduction of 45% in tear-film-caused error (corresponding to the reduction of capillary force, created by the tear-film) as a result of increasing the contact angle between the applanating prism surface and the cornea, averaged over the tear-film meniscus separating the applanating prism surface and the corneal surface (when using the CATS tonometer prism instead of the GAT tonometer prism).

Generally, however, in related embodiments, the reduction (of the tear-film adhesion-caused error, of a typical measurement performed with the use of a GAT tonometer tip) attributed to the use of the CATS tonometer tip instead of the GAT tonometer tip is at least 10%, preferably at least 20%, more preferably at least 30%, even more preferably by at least 40%, and even more preferably by at least 50%.

Empirical testing with the use of cadaver eye, extrapolated to a zero IOP, also validated the reduction in tear film adhesion force measured with the use of the CATS tonometer prism and the convention, flat-surfaced tonometer prism. The separation of a tonometer prism from a manometrically fluid filled cadaver eye simultaneously measures both the tear-film adhesion and the intraocular pressure (IOP) on the prism face over a dynamically reducing applanation area. Therefore, this dynamic process is not suitable to directly measure the isolated tear-film separation at full applanation and indicates a falsely low separation force. For this reason, the static tear-film separation conditions using the simulated corneas with PMMA hemi-spheres 1510 are likely to be more accurate. The 95% intervals for the extrapolated mean tear-film adhesion error to the 0-mmHg IOP cadaveric eye 1610 do not overlap the 95% intervals for mean film adhesion error from the acrylic cornea data. However, the results shows that the second-order curvilinear fit did trend towards the film adhesion error values from the acrylic cornea experiments as IOP approached 0-mmHg.

The use of an embodiment of the invention, therefore, provides a method for increasing an accuracy of measurement of IOP of the eye with the use of applanation tonometer system. Such method includes the step of performing the IOP measurement with the use of a CATS tonometer tip a contact surface of which is dimensioned to include first and second areas. The first area is configured as a concave portion centered on an axis of the tonometer tip, while the second area is dimensioned as an annular convex portion surrounding the first are and tangentially merging with the first area. The method further includes the step of acquiring first data representing the IOP, where the first data contains an error that is caused by the tear-film adhesion between the CATS tonometer tip and the surface of the eye and that is reduced by at least 10% with respect to the similar error contained in second data, the second data representing the IOP acquired with the use of a GAT tonometer tip.

Schematic of an Applanation Tonometer Measurement System.

Figure 4:
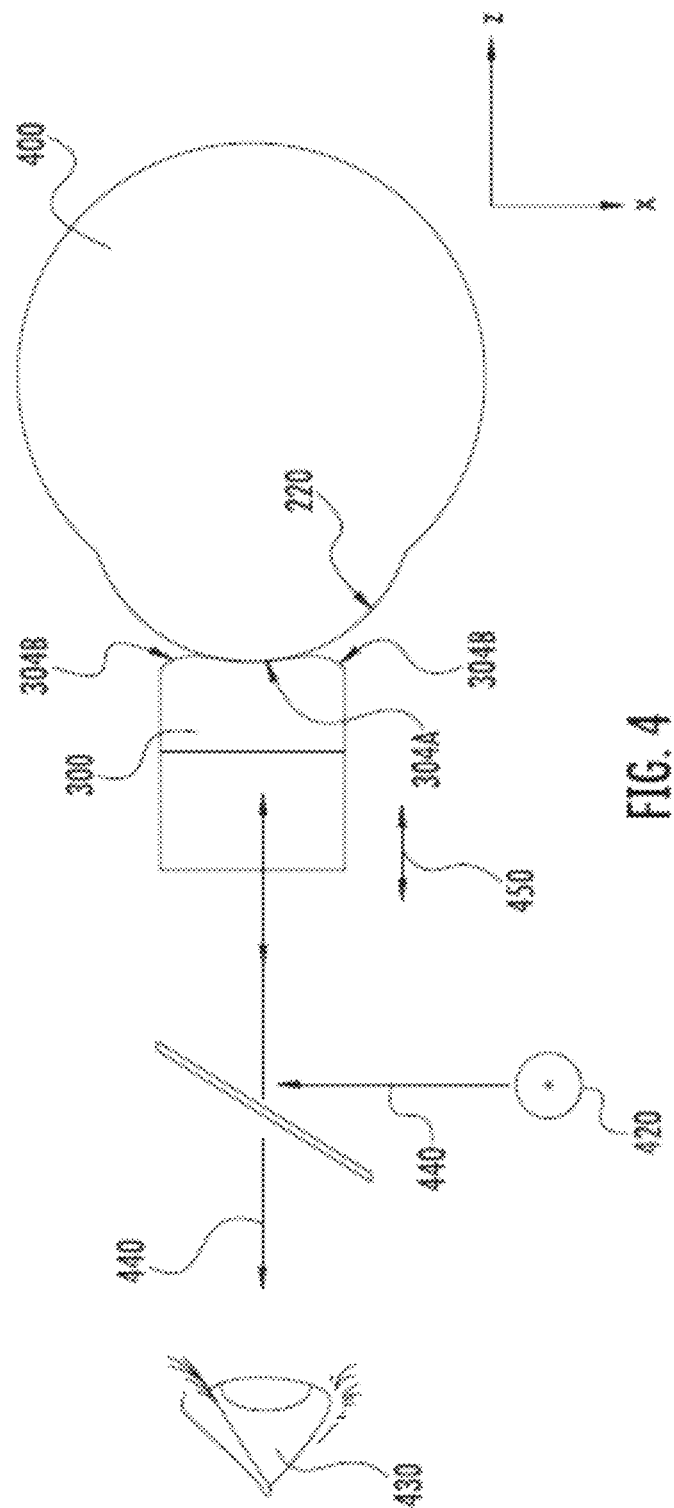
FIG. 4 is a diagram illustrating a method for measurement of intraocular pressure with an embodiment of the tip of FIGS. 3A, 3B.

A schematic diagram of FIG. 4 illustrates a process of the examination of an eye 400 with a tonometer a tip of which is configured according to the embodiment 300 of FIGS. 3A, 3B. (A similar process of examination would be carried out with the embodiment 500 or with a conventional GAT tonometer tip). During the measurement of the IOP, the corneal contact member 300 (having the surface 304 or the surface 350) is brought in contact with the corneal surface 220. The cornea-contacting surface 304 (or surface 350), of the member 300 is shaped according to a corresponding embodiment of the invention and dimensioned to minimize the deformation of the corneal surface 220 during the IOP-measurement procedure with the use of a Goldmann tonometer. In particular, and as will be understood by a skilled artisan, the minimization of the corneal deformation translates to minimization of the contribution of the corneal stiffness into the force defined by the eye in response to the applied measurement of the force (that, in turn, is required for proper applanation of a portion of the corneal surface that defines a circular area with a diameter of about 3.06 mm). As a practical result of such reduction or minimization of the corneal contribution, the correction factor (which takes into account corneal thickness and that is used to practically unreliable compensate for the unknown corneal stiffness, as discussed above) becomes substantially negligible. The computational compensation of the errors of the measurement of the IPO, therefore, becomes practically unnecessary. Similarly, a need to perform costly and time-consuming pachymetries, directed to correcting a cornea-thickness-related error that accompanies conventionally performed measurements of the IPO with the use of the Goldmann tonometer, is substantially eliminated, thereby leading to a measurement method that does not include pachymetry.

In further reference to FIG. 4, some components of the overall applanation tonometer system are omitted for the simplicity of illustration. The path of light, traversing the bi-prism-containing corneal contact member 300 on its propagation from a light source 420, to a reflecting element 424, to the surface 220 of the cornea (and, in reflection, to an observer 430) is designated with arrows 440. A variable pressure force, applied to the corneal surface 220 is designated with an arrow 450.

Assessment of Bias Between CATS and Conventional, Flat-Surfaced Tonometer Tips.

Figure 21:
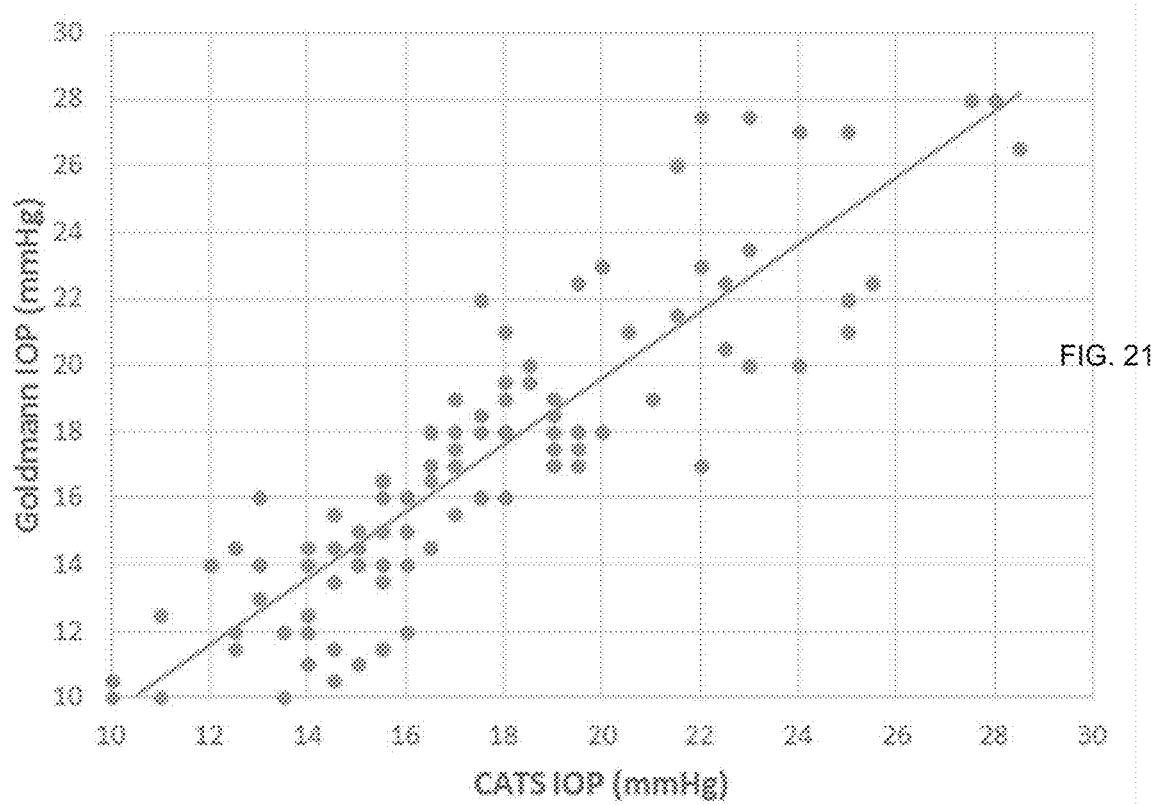
FIG. 21 is a plot illustrating correlation between the measurements of IOP performed with the embodiment of the invention and a conventional, flat-surfaced tonometer tip.

The IOP measurements with the use of GAT tonometer tip (conventional Goldmann tip, embodiment 100) and the CATS tonometer tip (embodiment 300) were directly compared over all IOP values to examine bias between the two tips. The results, shown in FIG. 21, confirm that the average measurement does not deviate significantly from a 1:1 IOP correlation with a coefficient of about 0.78. This result indicates the average bias between the GAT and CATS measurements is negligible at least over a range of pressures from 10 to 28 mm Hg. Accordingly, only the corneal biomechanical error parameters and/or errors caused by the tear-film adhesion significantly correlate to a difference between the GAT and CATS prism measurement results. A multiple regression analysis was completed (Dof=3, 95% CI). The multiple regression correlation coefficient with the three sources of corneal biomechanical errors (thickness, rigidity, and curvature) was $R^2=0.43$, which is similar to other studies examining IOP correlations. The ANOVA analysis of the multiple regression produced a value, of F-test of significance, of less than 0.01. The probabilities of null significance with each of the independent variables in the multiple regression were: p=0.02 for central corneal thickness, p=0.14 for corneal resistance factor, and p=0.19 for corneal curvature. As will be understood by a person of skill in the art, the corneal resistance factor of a measure of global corneal rigidity calculated based on corneal hysteresis data (here—acquired from the ocular response analyzer made by Reichert, Inc.) The variance in repeated IOP measurements indicated a minimal variance of 0.27 (standard deviation=0.52 mmHg) for the measurements performed with the CATS prism and 0.19 (standard deviation=0.44 mmHg) for the measurements performed with the conventional, flat-surfaced GAT prism.

As of to-date, clinicians almost universally have the capability to measure IOP with an applanating tonometer equipped with the tip configured according to a conventional, GAT-type embodiment 100 (which has the planar cornea-contacting surface), and a majority of clinicians consider it to be the most accurate measurement of IOP. The Goldmann applanation tonometer system with the GAT tonometer tip is used as the reference tonometer by the FDA, and it is a recognized protocol if IOP measurement by other devices is questionable. However, measurement errors and imprecisions resulting from the so-performed IOP measurement are well known to most clinicians. Current clinical practice does not correct for errors due to corneal rigidity, curvature and tear film adhesion, for example. However, the use of an embodiment of the disclosed invention—that is, an applanation tonometer system equipped with the CATS tonometer tip—convincingly demonstrated the capacity to avoid or reduce and/or correct for errors, and can provide a single error-corrected measurement without the use of additional corrective measurements, calculations, or interpretations of error.

The studies discussed above empirically indicated a significant reduction in sensitivity of the applanation tonometric measurements of IOP to various corneal biomechanical errors and tear-film adhesion cause errors when the applanation tonometer is equipped with the CATS tip (and as compared with the use of a conventionally-structured Goldmann applanation tonometer to perform the same measurements). The results confirm the CATS prism function including the force to pressure conversion supplied by the GAT or Perkins armature remains unchanged. This result is supported by the IOP zero measurement difference between the CATS and GAT prisms under average corneal biomechanical conditions. Also the direct comparison of IOP measurements between the two prisms averaged over all IOP's indicated a 1:1 correlation further supporting the lack of bias between the two tonometer prisms. The previously published study included cadaver eyes which also indicated negligible bias between the two prisms when compared to intracameral transducer measured IOP.

The combined error in IOP measurement in data can total +/−15 to 19 mm Hg for patients at the extremes of the ranges if corneal thickness, rigidity, curvature, and tear film. The most common recognized measurement error is due to central corneal thickness (CCT) at +/−7 mmHg or so, which is portion of the total potential error and may render CCT correction alone clinically inaccurate. However, for simplicity's sake, if only CCT-related error correction of +/−7 mmHg is considered (for the measurements conventionally performed with the flat-surfaced tonometer tip) in a standard distribution of varying central corneal thicknesses in a general population at risk for glaucoma, then the percent of the population with CCT errors greater than +/−2 mm Hg can be determined. Using the study's CCT population distribution, the percentage of people in which the IOP error is greater than +/−2 mm Hg translates to about 46% of all patients from accounting to CCT-related measurement error alone. Using the CATS tonometer prism and the predicted decrease in CCT sensitivity demonstrated by the studies discussed above, the number of patients' with an error greater than +/−2 mm Hg is reduced to about 3%. The use of CATS tonometer prism will likely negate the need for a pachymetry measurement with CCT-error correction, and it simultaneously corrects for other potentially more significant errors as well.

Notably, a surface of the tonometer tip used in the applanation tonometry apparatus typically has to be centered, with respect to the cornea with which such tip is brought in contact, to accurately measure IOP. While the decentration of the conventionally flat-surfaced GAT tip 100 does not prevent the measurements, the person of skill in the art will readily recognize that such decentration—while not being easily discovered or recognized (as the applanated mires, see 210A, 210B in FIG. 2B, see also FIG. 14C) are imaged through the flat-surfaced tip anywhere on the flat tip face)—substantially reduces both the quality and accuracy of the measurement. In stark contradistinction with the conventional tip, the CATS tonometer tip 300 is self-centering, in operation. The immediate recognition of possible decentration of the CATS tip with respect to the cornea stems from the concave shape of the central portion of the-surface (304A, 304B or 354A, 354B) of the tip, which simply does not allow the semicircular mires (semicircular parts of an image of applanated cornea) procured through such tip to intersect unless the CATS tip is centered on the axis of the cornea: the contact of two curved surfaces (that of the cornea and that of the CATS tonometer tip) produces a circle (and circular mires) if and only if the center of the contact area—a mutual point for both surfaces—is located at the axis of the cornea that connects the centers of curvatures of these surfaces.

Accordingly, the adjacent to one another ends of the mires (formed as parts of image of the applanated portion of the cornea in light transmitted through the CATS tip) can be made to substantially coincide only when an axis of the CATS tonometer tip and an axis of the cornea substantially coincide. In clinical practice, the CATS tip was easily centered by all of the investigators during the study and all measurements were serially repeatable demonstrating an equally low repeat measurement variance with both the conventionally-shaped and CATS tips.

The above-described stark distinction in operation, caused by differences between the surface profiles of the conventional, flat-surfaced tonometer tip and the CATS tonometer tip, defines an embodiment of a method for measurement of intraocular pressure with an applanating tonometer, which includes the step of i) pressing an axial portion of a cornea-contacting curvilinear surface of a first tonometer tip against cornea of an eye to define a first surface of contact between the curvilinear surface and the cornea and to cause first intra-corneal stress at a perimeter of the first area. (Here, the first tonometer tip has a first axis, and a value of the first intra-corneal stress is smaller than a value of second intra-corneal stress that occurs at a perimeter of a second surface of contact. The second surface is a surface of contact between a planar cornea-contacting surface of a second tonometer tip and the cornea formed as a result of pressing the planar cornea-contacting surface against the cornea.) The method further includes the steps of ii) forming a first image of the first area of contact in light transmitted twice through the first tonometer tip and reflected from the cornea (the first image including first and second semicircular portions) and iii) changing a force applied by the first tonometer tip to the cornea to achieve a condition when adjacent ends of the first and second semicircles substantially coincide, while such condition can be achieved only when an axis of the first tonometer tip and an axis of the cornea substantially coincide. In addition, the method may further include the step of iv) readjusting at least one of a position and orientation of the curvilinear surface with respect to the cornea if the condition is not achieved and repeating said changing.

It is understood that specific numerical values, chosen for illustration of examples of embodiments described in reference to FIGS. 3A, 3B, and 4, may generally vary over wide ranges to suit different applications. It will be understood by those of ordinary skill in the art that modifications to, and variations of, the illustrated embodiments may be made without departing from the inventive concepts disclosed herein. Both of the central concave surface portion and the associated peripheral surface portion of the corneal contact surface may be uninterrupted and spatially continuous (such as the portions 304A, 304B of FIGS. 3A, 3B or the portions 354A, 354B of FIG. 3C, for example). Alternatively, at least one of the central concave portion and the associate peripheral surface portion may be spatially discontinuous (at least in one direction transverse to the optical axis of the corneal contact member) such as to define, in a projection onto a plane perpendicular to the optical axis of the corneal contact member, a segmented footprint of the corneal contact surface. For example, at least one of the central concave surface portion and the peripheral surface portion may be spatially interrupted such as to preserve symmetry of such interrupted surface portion(s) with respect to at least one spatial axis. In reference to FIGS. 3A, 3B, and as a specific example, the peripheral surface portion 304B may be spatially interrupted along the y-axis. In operation, when pressed against the cornea, such segmented structure will define a plurality of applanation areas that are located substantially symmetrically about an axis along which the surface interruption is present (in this case, along the y-axis).

Overall, the use of a tonometer tip the corneal-contacting surface of which is formatted to deviate from the flat, planar surface and configured as including a curved surface having two having curvatures of opposite signs, as described above, have been demonstrated to increase the accuracy of the IOP measurement over those performed with the conventionally-used GAT that employs the tonometer tip with the flat surface and to at least reduce a need in and value of correction of the results of the measurement to take into account at least one of the central corneal thickness (or CCT), corneal rigidity or stiffness, corneal curvature, and/or intracorneal stress.

References throughout this specification to "one embodiment," "an embodiment," "a related embodiment," or similar language mean that a particular feature, structure, or characteristic described in connection with the referred to "embodiment" is included in at least one embodiment of the present invention. Thus, appearances of the phrases "in one embodiment," "in an embodiment," and similar language throughout this specification may, but do not necessarily, all refer to the same embodiment. It is to be understood that no portion of disclosure, taken on its own and in possible connection with a figure, is intended to provide a complete description of all features of the invention. Within this specification, embodiments have been described in a way that enables a clear and concise specification to bet written, but it is intended and will be appreciated that embodiments may be variously combined or separated without parting from the scope of the invention. In particular, it will be appreciated that all features described herein at applicable to all aspects of the invention.

When the present disclosure describes features of the invention with reference to corresponding drawings (in which like numbers represent the same or similar elements, wherever possible), the depicted structural elements are generally not to scale, and certain components are enlarged relative to the other components for purposes of emphasis and understanding. It is to be understood that no single drawing is intended to support a complete description of all features of the invention. In other words, a given drawing is generally descriptive of only some, and generally not all, features of the invention. A given drawing and an associated portion of the disclosure containing a description referencing such drawing do not, generally, contain all elements of a particular view or all features that can be presented is this view, at least for purposes of simplifying the given drawing and discussion, and directing the discussion to particular elements that are featured in this drawing. A skilled artisan will recognize that the invention may possibly be practiced without one or more of the specific features, elements, components, structures, details, or characteristics, or with the use of other methods, components, materials, and so forth. Therefore, although a particular detail of an embodiment of the invention may not be necessarily shown in each and every drawing describing such embodiment, the presence of this particular detail in the drawing may be implied unless the context of the description requires otherwise. In other instances, well known structures, details, materials, or operations may be not shown in a given drawing or described in detail to avoid obscuring aspects of an embodiment of the invention that are being discussed. Furthermore, the described single features, structures, or characteristics of the invention may be combined in any suitable manner in one or more further embodiments.

Moreover, if the schematic flow chart diagram is included, the depicted order and labeled steps of the logical flow are indicative of one embodiment of the presented method. Other steps and order of steps may be conceived that are equivalent in function, logic, or effect to one or more steps, or portions thereof, of the illustrated method. Without loss of generality, the order in which processing steps or particular methods occur may or may not strictly adhere to the order of the corresponding steps shown.

The invention as recited in claims appended to this disclosure is intended to be assessed in light of the disclosure as a whole, including features disclosed in prior art to which reference is made.

For the purposes of this disclosure and the appended claims, the use of the terms "substantially", "approximately", "about" and similar terms in reference to a descriptor of a value, element, property or characteristic at hand is intended to emphasize that the value, element, property, or characteristic referred to, while not necessarily being exactly as stated, would nevertheless be considered, for practical purposes, as stated by a person of skill in the art. These terms, as applied to a specified characteristic or quality descriptor means "mostly", "mainly", "considerably", "by and large", "essentially", "to great or significant extent", "largely but not necessarily wholly the same" such as to reasonably denote language of approximation and describe the specified characteristic or descriptor so that its scope would be understood by a person of ordinary skill in the art. The use of this term in describing a chosen characteristic or concept neither implies nor provides any basis for indefiniteness and for adding a numerical limitation to the specified characteristic or descriptor. As understood by a skilled artisan, the practical deviation of the exact value or characteristic of such value, element, or property from that stated may vary within a range defined by an experimental measurement error that is typical when using a measurement method accepted in the art for such purposes. For example, a reference to a vector or line or plane being substantially parallel to a reference line or plane is to be construed as such vector or line extending along a direction or axis that is the same as or very close to that of the reference line or plane (with angular deviations from the reference direction or axis that are considered to be practically typical in the art, for example between zero and fifteen degrees, more preferably between zero and ten degrees, even more preferably between zero and 5 degrees, and most preferably between zero and 2 degrees). A term "substantially-rigid", when used in reference to a housing or structural element providing mechanical support for a contraption in question, generally identifies the structural element that rigidity of which is higher than that of the contraption that such structural element supports. As another example, the use of the term "substantially flat" in reference to the specified surface implies that such surface may possess a degree of non-flatness and/or roughness that is sized and expressed as commonly understood by a skilled artisan in the specific situation at hand. For example, the terms "approximately" and about", when used in reference to a numerical value, represent a range of plus or minus 20% with respect to the specified value, more preferably plus of, minus 10%, even more preferably plus or minus 5%, most preferably plus or minus 2%.

The above disclosure described features of the invention with reference to corresponding drawings, in which like numbers represent the same or similar elements wherever possible. In the drawings, the depicted structural elements are generally not to scale, and certain components are enlarged relative to the other components for purposes of emphasis and understanding. It is to be understood that no single drawing is intended to support a complete description of all features of the invention. In other words, a given drawing is generally descriptive of only some, and generally not all, features of the invention. A given drawing and an associated portion of the disclosure containing a description referencing such drawing do not, generally, contain all elements of a particular view or all features that can be presented is this view, for purposes of simplifying the given drawing and discussion, and to direct the discussion to particular elements that are featured in this drawing. A skilled artisan will recognize that the invention may possibly be practiced without one or more of the specific features, elements, components, structures, details, or characteristics, or with the use of other methods, components, materials, and so forth. Therefore, although a particular detail of an embodiment of the invention may not be necessarily shown in each and every drawing describing such embodiment, the presence of this detail in the drawing may be implied unless the context of the description requires otherwise. In other instances, well known structures, details, materials, or operations may be not shown in a given drawing or described in detail to avoid obscuring aspects of an embodiment of the invention that are being discussed. Furthermore, the described single features, structures, or characteristics of the invention may be combined in any suitable manner in one or more further embodiments.

The invention as recited in claims appended to this disclosure is intended to be assessed in light of the disclosure as a whole, including features disclosed in prior art to which reference is made. Accordingly, the invention should not be viewed as being limited to the disclosed embodiment(s).

The invention claimed is:

1. A method for measurement of intraocular pressure (IOP) with a contact tonometer, the method comprising:
    pressing an axial portion of a cornea-contacting curvilinear surface of a first tonometer tip against the cornea of an eye to apply a force to the cornea and to define a first surface of contact with the cornea-contacting curvilinear surface,
        wherein the first tonometer tip has a first axis and the cornea has a corneal axis,
    forming a first image of the first surface of contact in light transmitted twice through the first tonometer tip and reflected from the cornea, the first image including first and second substantially semicircular portions,
    adjusting the force applied by the first tonometer tip to the cornea to achieve a condition when adjacent ends of said first and second semicircular portions substantially coincide,
        wherein said condition is achieved only when the first axis and the corneal axis substantially coincide.

2. The method according to claim 1, further comprising: if the condition is not achieved, realigning the cornea-contacting curvilinear surface with respect to the cornea and repeating said adjusting.

3. The method according to claim 1, wherein said pressing the axial portion of the cornea-contacting curvilinear surface includes pressing said axial portion having a first curvature with a first sign of curvature that is equal to a sign of curvature of the cornea.

4. The method according to claim 1, further comprising: reversibly changing a surface area of the first surface of contact by the adjusting the force.

5. The method according to claim 1, further comprising:
    determining a first value of the IOP with a use of said first image, at a moment when the adjacent ends substantially coincide, wherein a first error is smaller than a second error,
    the first error being an error contributed to said first value by any of misalignment between the first axis and the corneal axis and an effect produced by presence of a film of fluid between the cornea-contacting curvilinear surface,
    the second error representing an error contributed to a second value of the IOP measured with the contact tonometer equipped with a second tonometer tip, the second tonometer tip having a planar cornea-contacting surface.

6. A device for determining intraocular pressure (IOP) of an eye with a use of contact tonometry, the device comprising:
    a first tonometer tip having
        a first axis;
        a front surface having a central portion that is non-planar and has a non-zero curvature, and that is configured to applanate the cornea of the eye to form an applanated portion of the cornea when pressed against the cornea while reducing a first error as compared with a second error,
            wherein the cornea has a corneal axis;
            wherein the first error is an error contributed to a first value of a determined IOP of the eye by adhesion between the front surface and the cornea,
            wherein the second error is an error contributed to a second value of the IOP measured with the use of a second tonometer tip that has a planar cornea-contacting surface, and
            wherein the adhesion is caused by a film of fluid present between the front surface and the cornea; and
        a back surface that is substantially transverse to the first axis.

7. The device according to claim 6, further comprising:
    a system of optical prisms in a body of the first tonometer tip,
        wherein the optical prisms are disposed to form an image of the applanated portion of the cornea in light transmitted through the front surface and through the system of the optical prisms,
        wherein the image contains a first semicircle having a first end and a second semicircle having a second end,
        wherein the first end and the second end substantially coincide only when the first axis and the corneal axis substantially coincide.

8. The device according to claim 6, wherein said front surface is dimensioned to applanate the cornea, when pressed against the cornea, while reducing a third error as compared with a fourth error,
    wherein the third error is an error contributed to the first value of the determined IOP by misalignment between the first axis and the corneal axis,
    wherein the fourth error is an error contributed to the second value of the IOP.

9. The device according to claim 6, wherein a sign of the non-zero curvature is equal to a sign of a curvature of the cornea and a reduction of the first error, contributed to the first value of the determined IOP of the eye by the adhesion, is at least 10 percent of the first error.

10. The device according to claim 6, wherein the front surface includes an annular portion that circumscribes the central portion,
the annular portion tangentially merging with the central portion along a closed curve, the annular portion defining an axially-symmetric curve in a surface of the annular portion,
said axially-symmetric curve containing a plurality of vertices of the annular portion,
wherein a diameter of the axially-symmetric curve defines a maximum extent of the applanated portion of the cornea that can be achieved without forming a kink in the cornea.

11. The device according to claim 6, wherein the front surface is an azimuthally symmetric bi-curved surface having a cross-section, in a plane containing the first axis, that is defined by an axially-monotonic curve that is differentiable at every point of said curve.

12. A device for determining an intraocular pressure (IOP) of an eye with a use of contact tonometry, the device comprising:
a first tonometer tip having a first axis and a front surface, the front surface including:
a central portion that is non-planar, that has a non-zero curvature, and that is configured to applanate the cornea of the eye to form an applanated portion of the cornea when pressed against the cornea while having a first error reduced as compared with a second error, the cornea having a corneal axis,
wherein the first error is an error contributed to a first value of the IOP of the eye by adhesion between the front surface and the cornea, the first value being a value of the IOP tonometrically determined with a use of said first tonometer tip,
wherein the second error is an error contributed to a second value of the IOP measured with the use of a second tonometer tip that has a planar cornea-contacting surface, and
wherein the adhesion is caused by a film of fluid present between the front surface and the cornea;
wherein the central portion has a first curvature with a first sign, the cornea has a curvature of the cornea with a second sign, and the first sign is equal to the second sign.

13. The device according to claim 12, wherein said front surface is dimensioned to applanate the cornea of the eye, when pressed against the cornea, while reducing a third error as compared with a fourth error,
wherein the third error is an error contributed to the first value of the IOP by any of the curvature of the cornea, a thickness of the cornea, corneal rigidity, and misalignment between the first axis and the corneal axis,
wherein the fourth error is an error contributed to the second value of the IOP with the use of the second tonometer tip that has the planar cornea-contacting surface.

14. The device according to claim 12,
wherein the front surface further includes an annular portion surrounding the central portion and tangentially merging with the central portion along a closed plane curve, the annular portion having a curvature with a third sign, the third sign being opposite to the first sign.

15. The device according to claim 14,
wherein the annular portion contains an axially-symmetric curve in a surface of the annular portion,
said axially-symmetric curve containing a plurality of vertices of the annular portion,
wherein a diameter of the axially-symmetric curve defines a maximum extent of the applanated portion of the cornea.

16. The device according to claim 12, and further comprising:
a system of optical prisms in a body of the first tonometer tip,
wherein the optical prisms are disposed to form an image of the applanated portion of the cornea in light transmitted through the front surface and through the system of the optical prisms,
wherein the image contains a first semicircle having a first end and a second semicircle having a second end,
wherein the first end and second end substantially coincide only when the first axis and the corneal axis substantially coincide.

17. The device according to claim 12,
wherein the central portion contains an axially-symmetric curve in a surface of the central portion,
said axially-symmetric curve containing a plurality of vertices of the central portion,
wherein a diameter of the axially-symmetric curve defines a maximum extent of the applanated portion of the cornea achievable without forming a spatial kink in the cornea as a result of establishing contact between the front surface and the cornea.

18. The device according to claim 12, configured as a contact Goldmann tonometer.

19. A method for measurement of intraocular pressure (IOP) with a contact tonometer, the method comprising:
applying a first force to the cornea of an eye by bringing an axial portion of a cornea-contacting curvilinear surface of a first tonometer tip in contact with the cornea
i) to define a first surface of contact between the cornea-contacting curvilinear surface and the cornea, and
ii) to cause first intra-corneal stress at a location of the cornea as a result of applanation of the cornea at the first surface,
wherein the first tonometer tip has a first axis and the cornea has a corneal axis,
forming a first image of the first surface of contact in light transmitted twice through the first tonometer tip and reflected from the cornea;
and
tonometrically measuring a first value of the IOP with a use of the first image,
wherein the axial portion has a first curvature having a first sign of curvature that is equal to a sign of curvature of the cornea, and
wherein a first value of the first intra-corneal stress is smaller than a second value of second intra-corneal stress that occurs at said location as a result of applanation of the cornea with a second tonometer tip having a flat cornea-contacting surface by applying the first force to the cornea with the flat cornea-contacting surface of the second tonometer tip.

20. The method according to claim 19,
wherein said tonometrically measuring includes measuring the first value with a first error that is smaller than a second error,
wherein the first error is contributed to said first value by any of misalignment between the first axis and the corneal axis, and an effect produced by presence of a film of fluid between the cornea-contacting curvilinear surface and the cornea, wherein the second error represents an error contributed to a second value of the IOP measured with the contact tonometer that is equipped with the second tonometer tip while applying the same the first force to the cornea with the flat cornea-contacting surface of the second tonometer tip.

* * * * *